United States Patent
Billen et al.

[11] Patent Number: 5,728,686
[45] Date of Patent: Mar. 17, 1998

[54] ALKYLXANTHINE PHOSPHONATES AND ALKYLXANTHINE PHOSPHINE OXIDES AND THEIR USE AS PHARMACEUTICALS

[75] Inventors: Günter Billen, Niedernhausen; Ismahan Okyayuz-Baklouti; Hiristo Anagnostopulos, both of Wiesbaden; Stefan Müllner, Hochheim, all of Germany

[73] Assignee: Hoechst Aktiengesellschaft, Frankfurt am Main, Germany

[21] Appl. No.: 741,591

[22] Filed: Oct. 31, 1996

[51] Int. Cl.$^6$ .............. A61K 31/675; C07F 9/6512
[52] U.S. Cl. ............ 514/81; 544/244; 558/187; 558/189
[58] Field of Search ............... 514/81; 544/244

[56] References Cited

FOREIGN PATENT DOCUMENTS

| | | |
|---|---|---|
| 3376193 | 2/1993 | Australia . |
| 0343133 | 11/1989 | European Pat. Off. . |
| 0632048 | 6/1994 | European Pat. Off. . |
| 9620710 | 7/1996 | WIPO . |

*Primary Examiner*—Mukund J. Shah
*Assistant Examiner*—Pavanaram K. Sripada
*Attorney, Agent, or Firm*—Finnegan, Henderson, Farabow, Garrett & Dunner, L.L.P.

[57] ABSTRACT

Alkylxanthine phosphonates and alkylxanthine phosphine oxides and their use as pharmaceuticals A compound of the formula

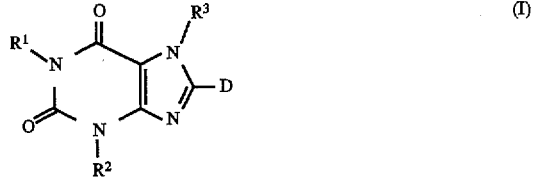

where $R^1$ and $R^3$ are identical or different and at least one of the radicals $R^1$ and $R^3$ is a radical of the formula XI

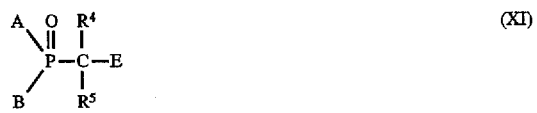

in which E is a covalent bond or a $(C_1-C_5)$-alkyl, are suitable for the production of pharmaceuticals for the treatment of muscular atrophy, cachexia, muscular dystrophy, sepsis, septic shock, endotoxic shock, systemic inflammation response syndrome, adult respiratory distress syndrome, cerebral malaria, chronic pneumonia, pulmonary sarcoidosis, reperfusion damage, scar formation, inflammation of the bowel and ulcerative colitis, as a result of infections, acquired immune deficiency syndrome, cancer, trauma and other disorders having increased protein loss, peripheral circulatory disorders, disorders having altered leucocyte adhesion, and also disorders which are accompanied by an increased or unregulated tumor necrosis factor production such as rheumatoid arthritis, rheumatoid spondylitis, osteoarthritis and other arthritic disorders.

17 Claims, No Drawings

ALKYLXANTHINE PHOSPHONATES AND ALKYLXANTHINE PHOSPHINE OXIDES AND THEIR USE AS PHARMACEUTICALS

The present invention relates to xanthine derivatives having at least one alkylphosphonate or alkylphosphine oxide group in the 1- or 7-position. These compounds are suitable for the treatment of muscular atrophy, muscular dystrophy, cachexia, sepsis, septic shock, endotoxic shock, systemic inflammation response syndrome (SIRS), adult respiratory distress syndrome (ARDS), cerebral malaria, chronic pneumonia, pulmonary sarcoidosis, reperfusion damage, scar formation, inflammation of the bowel and ulcerative colitis, as a result of infections, acquired immune deficiency syndrome (AIDS), cancer, trauma and other disorders with increased protein loss, peripheral circulatory disorders, disorders with altered leucocyte adhesion, and also disorders which are associated with an increased or unregulated tumor necrosis factor (TNF) production such as rheumatoid arthritis, rheumatoid spondylitis, osteoarthritis and other arthritic disorders. Processes for the preparation of the xanthine derivatives according to the invention are furthermore described.

Some oxoalkyl- and hydroxyalkylxanthines promote the circulation and can be employed in mitochondrial myopathies (WO 87/00523).

No pharmaceuticals were known until now which make it possible to reduce the loss of function of the musculature occurring in many disorders. Known pharmaceuticals exhibit an increase in the protein mass or inhibition of protein degradation (EP 464 932; EP 516 594; Drugs of the Future 11:927–930, 1986) or show a shift of the protein/fat ratio in favor of the protein fraction (EP 375 791; EP 290 122; EP 254 856). However, this permits no direct conclusion on the function of the affected muscles and is also to be observed when no disorder is present.

Some of the compounds which can be used according to the invention are known, but their use as pharmaceuticals has not been recognized (J. Am. Chem. Soc. 77, pages 2386 to 2388 (1955)).

It has now been found that the compound of the formula I reduces the loss of function of the musculature occurring in various disorders, and clearly lowers the mortality due to lipopolysaccharide (LPS)-induced endotoxin shock. It has further been found that the compound of the formula I antagonizes the effects of the inflammatory mediators substance P (SP), leukotrien $D_4$ (LTD$_4$) and platelet activating factor (PAF), and also effects phosphodiesterase inhibition and is therefore particularly suitable for the prophylaxis and/or therapy of the abovementioned disorders.

The invention relates to a compound of the formula I

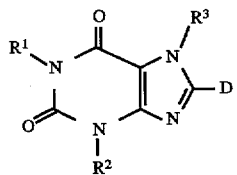

(I)

and/or a physiologically tolerable salt of the compound of the formula I and/or an optionally stereoisomeric form of the compound of the formula I, where $R^1$ and $R^3$ are identical or different and at least one of the radicals $R^1$ and $R^3$ is a) a radical of the formula XI

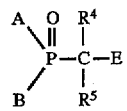

(XI)

in which $R^4$ and $R^5$ are identical or different and independently of one another are 1.1 a hydrogen atom,
1.2 hydroxyl or
1.3 ($C_1$–$C_6$)-alkyl, A and B are identical or different and independently of one another are 2.1 ($C_1$–$C_4$)-alkyl,
2.2 ($C_1$–$C_6$)-alkoxy,
2.3 hydroxyl or
2.4 benzyloxy, E is a covalent bond or a straight-chain or branched alkyl having 1 to 5 carbon atoms, and b) if only one of the radicals $R^1$ or $R^3$ have the meaning mentioned under a), the other radical $R^1$ or $R^3$ is 1) a hydrogen atom,
2) ($C_1$–$C_6$)-alkyl, straight-chain or branched,
3) ($C_2$–$C_6$)-alkyl, straight-chain or branched, where the carbon chain is interrupted by 1 or 2 oxygen atoms and 2 oxygen atoms bonded to one another are excluded,
4) ($C_1$–$C_8$)-alkyl, straight-chain or branched, substituted by
   4.1 an oxo group or
   4.2 one or two hydroxyl groups,
5) ($C_2$–$C_6$)-alkenyl, straight-chain or branched,
6) benzyl,
7) benzyl, mono-to pentasubstituted by
   7.1 ($C_1$–$C_4$)-alkyl or
   7.2 ($C_1$–$C_4$)-alkoxy,
8) ($C_3$–$C_6$)-cycloalkyl or
9) ($C_1$–$C_4$)-alkyl-($C_3$–$C_6$)-cycloalkyl, and $R^2$ is 1) a hydrogen atom,
2) ($C_1$–$C_6$)-alkyl, straight-chain or branched,
3) ($C_2$–$C_6$)-alkyl, straight-chain or branched, the carbon chain being interrupted by 1 or 2 oxygen atoms and 2 oxygen atoms bonded to one another being excluded,
4) benzyl,
5) benzyl, mono- to pentasubstituted by
   5.1 ($C_1$–$C_4$)-alkyl or
   5.2 ($C_1$–$C_4$)-alkoxy,
6) phenyl,
7) ($C_3$–$C_6$)-cycloalkyl or
8) ($C_1$–$C_4$)-alkyl-($C_3$–$C_6$)-cycloalkyl, and D is 1) a hydrogen atom or
2) a fluorine, chlorine, bromine or iodine atom, the compounds diethyl [4-(1,3-dimethylxanthin-7-yl)butyl] phosphonate, 5-(1,3-dimethoxyxanthin-7-yl) pentylphosphonic acid, 4-(1,3-dimethyl-xanthin-7-yl) butylphosphonic acid and 3-(1,3-dimethylxanthin-7-yl) propylphosphonic acid being excluded.

A compound of the formula I and/or a physiologically tolerable salt of the compound of the formula I and/or an optionally stereoisomeric form of the compound of the formula I is preferred, where A and B are 1) hydroxyl,
2) $C_2$-alkoxy or
3) methyl.

A compound is particularly preferred, where $R^2$ is
1) a hydrogen atom,
2) $(C_2-C_6)$-alkyl, straight-chain or branched, the carbon chain being interrupted by one oxygen atom,
3) benzyl,
4) cyclopropyl or
5) —$CH_2$-cyclopropyl.

A compound of the formula I is furthermore preferred, where one of the radicals $R^1$ or $R^3$ is a radical of the formula XI and the other radical $R^1$ or $R^3$ is
1) a hydrogen atom,
2) $(C_2-C_6)$-alkyl, straight-chain or branched, the carbon chain being interrupted by 1 or 2 oxygen atoms and 2 oxygen atoms bonded to one another being excluded,
3) benzyl or
4) —$CH_2$-cyclopropyl.

The invention furthermore relates to processes for the preparation of the compound of the formula I, an embodiment in this process consisting in
A) reacting a compound of the formula III

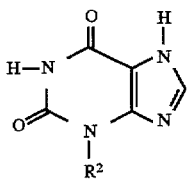

where $R^2$ has the meaning mentioned in formula I, in the presence of basic agents with an alkylating agent of the formula II

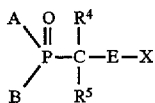

where X is chlorine, bromine, iodine or a sulfonic acid ester radical and $R^4$, $R^5$, A, B and E have the meaning mentioned in formula XI, to give a compound of the formula I, where $R^1$ is a hydrogen atom and $R^3$ is a radical of the formula XI

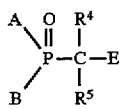

and $R^2$ has the meaning mentioned in formula I, or
B) reacting a compound of the formula I prepared according to A) in the presence of basic agents with an alkylating agent of the formula II, where X, $R^4$, $R^5$, A, B and E are defined as in process A), to give a compound of the formula I, where $R^1$ and $R^3$ are identical or different and are a radical of the formula XI, or
C) reacting a compound of the formula I prepared according to A) in the presence of basic agents with a compound $R^6$—X, where
$R^6$ is
1) a hydrogen atom,
2) $(C_1-C_6)$-alkyl, straight-chain or branched,
3) $(C_2-C_6)$-alkyl, straight-chain or branched, where the carbon chain is interrupted by 1 or 2 oxygen atoms and 2 oxygen atoms bonded to one another are excluded,
4) $(C_1-C_6)$-alkyl, straight-chain or branched, substituted by
4.1 an oxo group or
4.2 one or two hydroxyl groups,
5) $(C_2-C_6)$-alkenyl, straight-chain or branched,
6) benzyl,
7) benzyl, mono- to pentasubstituted by
7.1 $(C_1-C_4)$-alkyl or
7.2 $(C_1-C_4)$-alkoxy,
8) $(C_3-C_6)$-cycloalkyl or
9) $(C_1-C_4)$-alkyl-$(C_3-C_6)$-cycloalkyl, and X has the meaning mentioned under A), to give a compound of the formula I, where
$R^1$ has the meaning of $R^6$, $R^2$ is defined according to the compound of the formula I and $R^3$ has the meaning of the formula II, or
D) reacting a compound of the formula IV

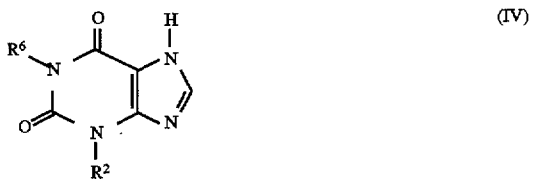

where $R^6$ has the meaning mentioned under C) and $R^2$ has the meaning mentioned in formula I, in the presence of basic agents with an alkylating agent of the formula II to give a compound of the formula I, where $R^1$ has the meaning of $R^6$, and $R^2$ has the meaning mentioned in formula I and $R^3$ has the meaning mentioned in formula XI, or
E) reacting a compound of the formula V

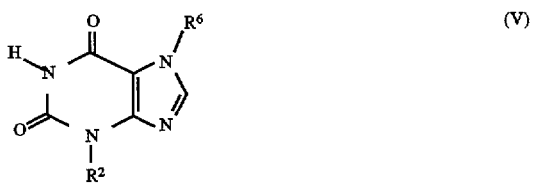

where $R^6$ has the meaning mentioned under C) and $R^2$ has the meaning mentioned in formula I, in the presence of basic agents with an alkylating agent of the formula II to give a compound of the formula I, where $R^1$ has the meaning mentioned in formula XI, $R^2$ has the meaning mentioned in formula I and $R^3$ has the meaning of $R^6$, or
F) in a compound of the formula I, where at least one $R^1$, $R^2$ and $R^3$ is a benzyl, alkoxymethyl or alkoxyalkoxymethyl radical and at least one $R^1$ and $R^3$ is a radical of the formula XI, removing the benzyl, alkoxymethyl or alkoxyalkoxymethyl radical from the formula I under reducing or hydrolytic conditions, or
G) reacting a compound of the formula VI

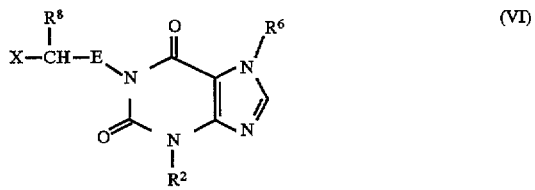

where
$R^6$ has the meaning mentioned under C),
$R^2$ has the meaning mentioned in formula I,
E has the meaning mentioned in formula XI, $R^8$ is a hydrogen atom or $(C_1-C_4)$-alkyl and X is chlorine, bromine, iodine or a sulfonic acid ester radical, in the presence of a strong base such as sodium hydride, butyllithium or lithium diisopropylamide in an inert solvent with a compound of the formula VIII

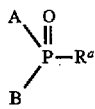 (VIII)

where A and B have the meaning mentioned in formula I and $R^a$ is a hydrogen atom or $(C_1-C_4)$-alkyl, to give a compound of the formula I, where $R^1$ has the meaning mentioned in formula XI, $R^2$ has the meaning mentioned in formula I and $R^3$ has the meaning of $R^6$, or H) reacting a compound of the formula VI, where $R^2$, $R^6$, $R^8$, E and X have the meaning mentioned under G), with a compound of the formula IX

 (IX)

where P is phosphorus, O is oxygen and $R^{10}$ is a $(C_1-C_4)$-alkyl, to give a compound of the formula I, where $R^1$ has the meaning mentioned in formula XI, $R^2$ has the meaning mentioned in formula I and $R^3$ has the meaning of $R^6$, or I) converting a compound of the formula I, where $R^1$, $R^2$, $R^3$, E and D have the meaning mentioned in formula I and A and B are $(C_1-C_4)$-alkyl or $(C_1-C_4)$-alkoxy, with agents such as mineral acids or silyl halides into the corresponding phosphonic acid derivatives of the formula I, or K) converting a compound of the formula I, where $R^1$, $R^2$, $R^3$, E and D have the meaning mentioned in formula I and A or B is a benzyloxy group, selectively into the corresponding phosphonic acid hemiesters, or L) halogenating a compound of the formula I, where $R^1$, $R^2$, $R^3$, E, A and B have the meaning mentioned in formula I and D is a hydrogen atom, a corresponding compound of the formula I being formed in which D is fluorine, chlorine, bromine or iodine, or M) isolating the compound of the formula I prepared according to processes A) to L) either in free form or, in the case of the presence of acidic or basic groups, optionally converting it into physiologically tolerable salts.

The preparation of the 3-alkyl-, 1,3-dialkyl- or 3,7-dialkylxanthines used as starting substances is for the greatest part known or they can be easily prepared by methods known from the literature (Ken-ichi Miyamoto et al., J. Med. Chem. 35 (1992), 4039-4344).

The reaction of the mono- or disubstituted xanthine derivatives of the formula III, IV or V with the alkylating agents of the formula II concerned or R6-X is usually carried out in a dispersant or solvent which is inert to the reaction participants. Those which are suitable are especially dipolar aprotic solvents, for example formamide, dimethylformamide, dimethylacetamide, dimethyl sulfoxide, acetone or butanone; however, alcohols such as methanol, ethylene glycol and its mono- or di($C_1-C_4$)alkyl ethers, ethanol, propanol, isopropanol and the various butanols; hydrocarbons such as benzene, toluene or xylenes; halogenated hydrocarbons such as dichloromethane, or chloroform; pyridine and also mixtures of the solvents mentioned or mixtures thereof with water can also be used.

The alkylations are expediently carried out in the presence of a basic agent. Those suitable are, for example, alkali metal or alkaline earth metal hydroxides, carbonates, hydrides or alkoxides and organic bases such as trialkylamines, quaternary ammonium or phosphonium hydroxides and crosslinked resins having fixed, optionally substituted ammonium or phosphonium groups. The xanthine derivatives, however, can also be employed directly in the form of their separately prepared salts, such as, for example, the alkali metal, alkaline earth metal or optionally substituted ammonium or phosphonium salts. The substituted xanthine derivatives can furthermore be easily alkylated with the additional aid of so-called phase-transfer catalysts.

The procedures described above are in general carried out at a reaction temperature of 0° C. up to the boiling point of the particular reaction medium used, preferably from 20° C. to 130° C., if appropriate at elevated or reduced pressure, but usually at atmospheric pressure, it being possible for the reaction time to be from less than one hour to several hours. The elimination of leaving groups with formation of the xanthines of the formula I according to the invention or their precursors is carried out under standard conditions, which have been developed, especially, in the context of the protective group technique in alkaloid and peptide syntheses and can thus be assumed to be largely known.

The benzyl group, which is optionally substituted in the phenyl ring, is then preferably removed by reduction. Beside chemical reaction with sodium in liquid ammonia, elimination by catalytic hydrogenation in the presence of a noble metal catalyst is preferably suitable for this purpose, the replacement of molecular hydrogen by formic acid or its salts, in this case in particular ammonium formate, having often proven suitable. The reaction medium used in this context is usually a lower alcohol, with addition of formic acid or ammonia; solvents, such as dimethylformamide or glacial acetic acid, but also mixtures thereof with water, can be used. Suitable hydrogenation catalysts are principally palladium and palladium hydroxide on activated carbon or barium sulfate, while other noble metals such as platinum, rhodium and ruthenium frequently give rise to side reactions on account of competing nuclear hydrogenation and can therefore only be employed to a limited extent. The hydrogenolysis is expediently carried out at temperatures from 20° to 100° C. and under atmospheric pressure or preferably slight overpressure of up to 10 bar, as a rule reaction times of a few minutes up to several hours being needed.

The substituted xanthines, which carry an alkoxymethyl group, are O, N-acetals and can accordingly be easily demasked under the customary conditions of acidic hydrolysis. The reaction is advantageously carried out with warming in dilute mineral acids, such as hydrochloric or sulfuric acid, if appropriate with addition of glacial acetic acid, dioxane, tetrahydrofuran or a lower alcohol as a solubilizer. Occasionally, perchloric acid or organic acids, such as trifluoroacetic, formic and acetic acid, are also suitable. In the case of acid-labile derivatives, the use of pyridinium tosylate (PPTS) has proven suitable. The reaction temperature should not exceed 60° C. during cleavage in mineral acid solution to avoid elimination. In principle, the cleavage of the ether group can also be carried out with the aid of Lewis acids such as zinc bromide and titanium tetrabromide, in anhydrous medium, preferably in dichloromethane or chloroform. Halogenation to give the 8-haloxanthines according to the invention is preferably carried out by reacting the corresponding xanthine with elemental halogen in a suitable solvent, for example methylene chloride, chloroform or carbon tetrachloride, preferably in glacial acetic acid.

The alkylating agents of the formula I1 used as precursors are for the largest part known (B. Helferich et al., Ann. 655 (1962), 59) or can easily be prepared in analogy to the methods known from the literature. The mixed phosphonic acid esters of the formula II, where A and B are not identical, can be prepared by reacting the methyl or ethyl esters of the corresponding phosphonic acids of the formula II with acid halides of inorganic acids such as thionyl chloride or phosphorus pentachloride in suitable, preferably halogenated, solvents to give the corresponding monoacid halides and converting these, after purification by distillation, into the corresponding mixed esters of the formula III, where A and B are not identical, with an alcohol in the presence of basic agents.

The preparation of physiologically tolerable salts from compounds of the formula I capable of salt formation, including their stereoisomeric forms, is carried out in a manner known per se. Thus phosphonic acids and phosphonic acid hemiesters form stable alkali metal, alkaline earth metal or optionally substituted ammonium salts with basic reagents such as hydroxides, carbonates, hydrogen carbonates, alkoxides and also ammonia or organic bases, for example trimethyl- or triethylamine, ethanolamine or basic amino acids such as lysine, ornithine or arginine.

The invention furthermore relates to a pharmaceutical comprising a compound of the formula I, wherein the compounds diethyl [4-(1,3-dimethylxanthin-7-yl)butyl] phosphonate, 5-(1,3-dimethylxanthin-7-yl)-pentylphosphonic acid, 4-(1,3-dimethylxanthin-7-yl) butylphosphonic acid and 3-(1,3-dimethylxanthin-7-yl) propylphosphonic acid are not excluded.

The invention furthermore relates to the use of the compound of the formula I for the preparation of pharmaceuticals for the prophylaxis and therapy of muscular atrophy, muscular dystrophy, cachexia, sepsis, septic shock, endotoxic shock, SIRS, ARDS, cerebral malaria, chronic pneumonia, pulmonary sarcoidosis, reperfusion damage, scar formation, inflammation of the bowel and ulcerative colitis, as a result of infections, AIDS, cancer, trauma and disorders having increased protein loss, peripheral circulatory disorders, disorders having altered leucocyte adhesion, and disorders which are associated with an increased or unregulated TNF production, such as rheumatoid arthritis, rheumatoid spondylitis, osteoarthritis and other arthritic disorders.

The invention also relates to a process for the production of a pharmaceutical, which comprises bringing at least one compound of the formula I into a suitable administration form using a pharmaceutically suitable and physiologically tolerable excipient and, if appropriate, other suitable active compounds, additives or auxiliaries.

The pharmaceuticals according to the invention, which as active compounds contain the compounds of the formula I, if appropriate in stereoisomerically pure form and/or as physiologically tolerable salts, either per se, for example in microcapsules, in mixtures with one another or preferably, in combination with suitable pharmaceutical excipients, diluents and/or other auxiliaries, can be administered intravenously, intramuscularly, parenterally, rectally or orally.

Suitable solid or liquid pharmaceutical preparation forms are, for example, granules, powders, coated tablets, tablets, (micro)capsules, suppositories, syrups, juices, suspensions, emulsions, drops or injectable solutions and also preparations having protracted release of active compound, in whose preparation auxiliaries, such as excipients, disintegrants, binders, coating agents, swelling agents, glidants or lubricants, flavorings, sweeteners or solubilizers, are customarily used. Frequently used auxiliaries which may be mentioned are, for example, magnesium carbonate, titanium dioxide, lactose, mannitol and other sugars, talc, lacto-protein, gelatine, starch, cellulose and its derivatives, animal and vegetable oils, such as fish liver oil, sunflower oil, groundnut oil or sesame oil, polyethylene glycols and solvents, such as, for example, sterile water, physiological saline solution and mono- or polyhydric alcohols, e.g. glycerol. In the case of the strongly acid-reacting phosphonic acid and phosphinic acids of formula I, the active compound is formulated such that it is present in salt form with a physiologically tolerable pH.

The pharmaceutical preparations are preferably prepared and administered in dose units, each unit comprising, as active constituent, a certain dose of at least one compound of formula I, if appropriate in stereoisomerically pure and/or salt form. In the case of solid dose units, such as tablets, capsules, coated tablets or suppositories, this dose can be up to approximately 1000 mg, but preferably approximately 100 to 600 mg, and in the case of injection solutions in ampoule form up to approximately 300 mg, but preferably approximately 20 to 200 mg. For the treatment of an adult patient of weight approximately 70 kg, depending on the efficacy of the compounds of formula I, daily doses of 50 to 3000 mg of active compound, preferably approximately 150 to 1000 mg, are indicated in the case of oral administration and approximately 50 to 1000 mg, preferably approximately 100 to 500 mg, in the case of intravenous administration. Under certain circumstances however, even higher or lower daily doses may be appropriate. The daily dose can be administered either by single administration in the form of an individual dose unit or else of several smaller dose units or by multiple administration of subdivided doses at certain intervals.

Finally, the compounds of the formula I, their optionally stereoisomeric forms and/or their physiologically tolerable salts can also be formulated together with other suitable active compounds, for example antithrombotics, androgens, anabolics, insulins, calcium channel blockers, plasma expanders and other vaso therapeutics, in the preparation of the abovementioned pharmaceutical preparation forms.

EXAMPLE 1

Diethyl [4-(1,3-dimethylxanthin-7-yl)butyl] phosphonate a) Diethyl 4-chlorobutanephosphonate $a_1$) from 1-bromo-4-chlorobutane:

A mixture of 342 g (2.0 mol) of 1-bromo-4-chlorobutane and 166.2 g (1.0 mol) of triethyl phosphite was heated for approximately 5 hours at an oil bath temperature of 130° C. while stirring and passing in nitrogen until approximately 109 g (1.0 mol) of bromoethane distilled over into a receiver strongly cooled with ice. The reaction mixture was distilled first in a bulb tube and then fractionally.

Yield: 137 g (59.9% of theory), boiling point (0.1 mbar) 145°–152° C. $C_8H_{18}ClO_3P$ (molecular weight (MW)= 228.7)

$a_2$) from diethyl phosphite:

A solution of sodium diethyl phosphite which had been prepared from the calculated amount of sodium hydride and 110.5 g of diethyl phosphite (0.8 mol) in absolute diethyl ether was added dropwise to a solution of 510 g (4.0 mol) of 1,4-dichlorobutane in 400 ml of boiling petroleum ether. After further heating under reflux and distilling off the readily volatile components, the sodium chloride formed was filtered off and the filtrate was distilled under reduced pressure.

Yield: 103 g (56.3% of theory), boiling point (0.1 mbar) 145°–152° C., $C_8H_{18}ClO_3P$ (MW=228.7)

b) Diethyl [4-(1,3-dimethylxanthin-7-yl)butyl] phosphonate 10.9 g (0.05 mol) of 1,3-dimethylxanthine were suspended in 150 ml of DMF, treated with 13.7 g (0.06 mol) of diethyl 4-chlorobutanephosphonate and 7.0 g (0.05 mol) of activated potassium carbonate and heated at 70° C. for approximately 4 hours. The solid was then filtered off, the filtrate was concentrated under reduced pressure and the oily residue which remained was taken up in ethyl acetate, filtered again and crystallized from diisopropyl ether.

Yield: 13.9 g (74% of theory), melting point: 122°–124° C., $C_{15}H_{25}N_4O_5P$ (MW=372.4), $^1$H-NMR (CDCl$_3$) δ=1.31 (t, 6H); 1.45–2.20 (m, 6H); 3.55 (s, 3H); 3.98 (s, 3H); 3.80–4.15 (m, 6H); 7.50 (s, 1H) ppm

EXAMPLE 2

Diethyl [4-(3-methylxanthin-7-yl)propyl] phosphonate a) Diethyl 3-bromopropanephosphonate A mixture of 605 g (3.0 mol) of 1,3-dibromopropane and 250 g (1.5 mol) of triethyl phosphite was heated at an oil bath temperature of 130° C., while stirring and passing in nitrogen, for approximately 5 hours until approximately 154 g (1.5 mol) of bromoethane distilled over into a strongly ice-cooled receiver. The reaction mixture was distilled first in a bulb tube and then fractionally.

Yield: 178 g (46% of theory), boiling point (1 mbar): 121°–125° C. $C_7H_{16}ClO_3P$ (MW=259.1)

b) Diethyl [4-(3-methylxanthin-7-yl)propyl]phosphonate 16.6 g (0.1 mol) of 3-methylxanthine were suspended in 250 ml of DMF, treated with 31 g (0.12 mol) of diethyl 3-bromopropanephosphonate and 16.5 g (0.12 mol) of activated potassium carbonate and heated at 90° C. for approximately 6 hours. The solid was then filtered off, the filtrate was concentrated under reduced pressure and the oily residue which remained was chromatographed on a silica gel column (eluent: ethyl acetate/methanol 10:1).

Yield: 4.5 g (13% of theory), melting point: 211° C., $C_{13}H_{21}N_4O_5P$ (MW=344.3), $^1$H-NMR (CDCl$_3$) δ=1.30 (t, 6H); 1.58–1.80 (m, 2H); 2.19–2.32 (m, 2H); 3.55 (s, 3H); 4.00–4.18 (m, 4H); 4.42 (t, 2H); 7.81 (s, 1H); 9.59 (s, 1H, NH) ppm

EXAMPLE 3

Diethyl [4-(3-methylxanthin-7-yl)butyl]phosphonate a) 7-Ethoxymethyl-3-methylxanthine 52.5 g (0.28 mol) of p-toluenesulfonyl chloride were initially introduced into 50 ml of dimethylformamide and 22.6 g (0.29 mol) of sodium acetate were introduced with stirring and ice-cooling. The mixture was subsequently stirred for one hour, treated with 39.1 g of formaldehyde diethyl acetal and again subsequently stirred for one hour. 41.5 g of 3-methylxanthine were then introduced and the reaction mixture was heated at 90° C. for 2 hours. After cooling to 10° C., the precipitated product was filtered off with suction, washed with a little dimethylformamide and washed with demineralized water until chloride-free. The crude product obtained was recrystallized from dimethylformamide.

Yield: 42.5 g (68.9% of theory), melting point: 262° C., $C_9H_{12}N_4O_3$ (MW=224.2)

b) 1-Benzyl-7-ethoxymethyl-3-methylxanthine 205 g (1.2 mol) of benzyl bromide were added to a suspension of 224 g (1 mol) of 7-ethoxymethyl-3-methylxanthine and 165 g of potassium carbonate in 1000 ml of dimethylformamide and the mixture was then stirred overnight at 90° C. The reaction solution was filtered hot, the filtrate was concentrated under reduced pressure and the residue was dried to constant weight in a bulb tube at 1 mbar and 60° C.

c) 1-Benzyl-3-methylxanthine hydrochloride

The unpurified 1-benzyl-7-ethoxymethyl-3-methylxanthine was treated with 1000 ml of 5N hydrochloric acid and stirred at 60° C. for 6 hours. The precipitated solid was filtered off with suction, washed with ethanol and dried under reduced pressure (164 g). It was possible from the mother liquor, after concentrating to approximately 50%, to isolate a further 35 g of the desired product.

Yield: 199 g (68% of theory), melting point: 227° C., $C_{13}H_{12}ClN_4O_2$ (MW=291.4)

d) Diethyl [4-(1-benzyl-3-methylxanthin-7-yl)butyl] phosphonate 20 g (0.078 mol) of 1-benzyl-3-methylxanthine hydrochloride, 21.4 g (0.094 mol) of diethyl 4-chlorobutanephosphonate and 26 g (0.2 mol) of potassium carbonate were suspended in 400 ml of dimethylformamide and stirred at 70° C. for 6 hours. The solution was filtered hot and the dimethylformamide was evaporated under reduced pressure. The oily residue which remained was taken up in dichloromethane and washed several times with water. After evaporating the solvent, it was possible to reuse the pale yellow, oily residue without purification.

Yield: 26 g (75% of theory), oil, $C_{21}H_{29}N_4O_5P$ (MW=448.5)

e) Diethyl [4-(3-methylxanthin-7-yl)butyl]phosphonate 13 g (0.03 mol) of diethyl [4-(1-benzyl-3-methylxanthin-7-yl)-butyl]phosphonate were suspended in 150 ml of ethanol with 2 g of palladium on activated carbon (10%) and, after addition of 3 ml of concentrated ammonia solution, hydrogenated with shaking at 1.5 bar in the course of 48 hours. The catalyst was filtered off, the solvent was evaporated under reduced pressure and the residue which remained was crystallized from diisopropyl ether.

Yield: 8.9 g (83% of theory), melting point: 160°–168° C., $C_{14}H_{23}N_4O_5P$ (MW=358.3), $^1$H-NMR (CDCl$_3$) δ=1.29 (t, 6H); 1.52–2.05 (m, 6H); 3.54 (s, 3H); 3.95–4.15 (m, 4H); 4.28 (t, 2H); 7.60 (s, 1H); 9.22 (s, 1H, b) ppm

EXAMPLE 4

Diethyl [4-(1-ethyl-3-methylxanthin-7-yl)butyl] phosphonate a) 7-Ethoxymethyl-1-ethyl-3-methylxanthine 30 g (0.134 mol) of 7-ethoxymethyl-3-methylxanthine were suspended in 500 ml of absolute DMF with 25 g (0.161 mol) of ethyl iodide and 22.2 g (0.161 mol) of potassium carbonate and the mixture was stirred at 70° C. for 5 hours. The solution was filtered and the residue which remained was crystallized in diisopropyl ether. 28.7 g (85% of theory) of the title substance were obtained and employed without purification in Example 4b).

b) 1-Ethyl-3-methylxanthine 28.7 g (0.11 mol) of 7-ethoxymethyl-1-ethyl-3-methylxanthine were stirred at 60° C. for 60 hours in a solution of 200 ml of 5N hydrochloric acid and 200 ml of ethanol. The reaction mixture was concentrated to dryness and the residue which remained was crystallized in ethyl acetate/diisopropyl ether.

Yield: 20.2 g (91% of theory), melting point: 212° C. $C_8H_{10}N_4O_2$ (MG=194.2)

c) Diethyl [4-(1-ethyl-3-methylxanthin-7-yl)butyl] phosphonate 9.7 g (0.05 mol) of 1-ethyl-3-methylxanthine were stirred at 70° C. for 6 hours with 12.7 g (0.06 mol) of diethyl chlorobutanephosphonate and 8.3 g of potassium carbonate. The solution was filtered, the solvent was evaporated, and the residue which remained was chromatographed (eluent: ethyl acetate/methanol 10:1) and crystallized from ethyl acetate/diisopropyl ether.

Yield: 7.2 g (38% of theory), melting point: 108° C., $C_{16}H_{27}N_4O_5P$ (MW=386.4), $^1H$-NMR ($CDCl_3$) $\delta$=1.23 (t, 3H); 1.28 (t, 6H); 1.55–2.05 (m, 6H); 3.55 (s, 3H); 3.95–4.15 (m, 6H); 4.28 (t, 2H); 7.52 (s, 1H) ppm

EXAMPLE 5

Diethyl [4-(1-(5-hydroxy-5-methylhexyl-3-methylxanthin-7-yl)butyl]-phosphonate 10 g (0.036 mol) of 5-hydroxy-5-methylhexyl-3-methylxanthine were stirred at 90° C. for 16 hours with 5 g of potassium carbonate and 9.9 g (0.043 mol) of diethyl chlorobutanephosphonate. The solution was filtered and concentrated and the residue which remained was chromatographed (eluent: dichloromethane/methanol 10:1).

Yield: 8.6 g (51% of theory), oil, $C_{21}H_{37}N_4O_5P$ (MW=472.5), $^1H$-NMR ($CDCl_3$) $\delta$=1.17 (s, 6H); 1.28 (t, 6H); 1.31–2.05 (m, 12H); 3.55 (s; 3H); 3.95–4.15 (m, 6H); 4.26 (t, 2H); 7.52 (s, 1H) ppm

EXAMPLE 6

Diethyl [4-(1-ethoxymethyl-3-methylxanthin-7-yl) butyl]phosphonate a) 7-Benzyl-3-methylxanthine 16.8 g (0.7 mol) of sodium hydride were introduced in portions with stirring into a suspension of 99.6 g (0.6 mol) of 3-methylxanthine in 1.5 l of dimethylformamide. After evolution of hydrogen had ended, the mixture was heated to 100° C., treated dropwise with 76 g (0.6 mol) of benzyl chloride and heated at 120° C. for a further 6 hours. The reaction mixture was cooled and cautiously poured into 3 l of water. The solid was filtered off with suction and washed with water, the filter residue was taken up in ethanol and the solution was stirred at room temperature for one hour. The crystallizate was filtered, washed with ethanol and dried under reduced pressure.

Yield: 90.7 g (59% of theory), melting point: 263° C. $C_{13}H_{12}N_4O_2$ (MW=256.3)

b) 7-Benzyl-1-ethoxymethyl-3-methylxanthine 20 g (0.078 mol) of 7-benzyl-3-methylxanthine were stirred at 80° C. for 6 hours with 8.8 g (0.094 mol) of ethoxymethyl chloride and 13 g of potassium carbonate in 500 ml of absolute dimethylformamide, the mixture was filtered and concentrated, and the residue which remained was chromatographed (eluent: dichloromethane/methanol 20:1).

Yield: 17.6 g (70% of theory), oil, $C_{16}H_{18}N_4O_3$ (MW=314.3)

c) 1-Ethoxymethyl-3-methylxanthine 17.5 g (0.056 mol) of 7-benzyl-1-ethoxymethyl-3-methylxanthine were hydrogenated over 1.8 g of palladium (10%) on activated carbon at room temperature for 8 hours in 500 ml of ethanol. The catalyst was filtered off and the filtrate was concentrated to dryness and crystallized from dimethylformamide/diisopropyl ether.

Yield: 7.9 g (63.4% of theory), melting point: 164°–168° C., $C_9H_{12}N_4O_3$ (MW=224.2)

d) Diethyl [4-(1-ethoxymethyl-3-methylxanthin-7-yl) butyl]phosphonate 4 g (0.018 mol) of 1-ethoxymethylxanthine were stirred at 70° C. for 6 hours with 3 g of potassium carbonate and 4.9 g (0.0214 mol) of diethyl chlorobutanephosphonate. The solution was filtered and concentrated, and the residue which remained was chromatographed (eluent: dichloromethane/methanol 20:1).

Yield: 5.2 g (69% of theory), oil, $C_{17}H_{29}N_4O_5P$ (MW=416.4), $^1H$-NMR ($CDCl_3$) $\delta$=1.20 (t, 3H); 1.28 (t, 6H); 1.53–2.05 (m, 6H); 3.55 (s, 3H); 3.66 (q, 2H); 3.95–4.15 (m, 4H); 4.28 (t, 2H); 5.46 (s, 2H); 7.54 (s, 1H) ppm

EXAMPLE 7

Diethyl 4-{7-[4-(diethoxyphosphoryl)butyl]-3-methylxanthin-1-yl}butyl-phosphonate 8 g (0.022 mol) of 7-(4-diethylphosphonobutyl)-3-methylxanthine (according to Example 24) were suspended in 100 ml of DMF, treated with 6.13 g (0.027 mol) of diethyl 4-chlorobutanephosphonate and 3.7 g (0.028 mol) of activated potassium carbonate and heated at 70° C. for 4 hours. The product was then filtered, the filtrate was concentrated under reduced pressure and the oily residue which remained was chromatographed on a silica gel column (eluent: ethyl acetate/methanol 10:1).

Yield: 9.1 g (74% of theory), oil, $C_{22}H_{40}N_4O_8P_2$ (MW=550.5), $^1H$-NMR ($CDCl_3$) $\delta$=1.27 (t, 12H); 1.50–2.05 (m, 12H); 3.55 (s, 3H); 3.88–4.17 (m, 1 OH); 4.28 (t, 2H); 7.64 (s, 1H) ppm

EXAMPLE 8

Diethyl [3-(1,3-dimethylxanthin-7-yl)propyl] phosphonate

The title substance was prepared from 1,3-dimethylxanthine and diethyl 3-bromopropanephosphonate analogously to Example 1.

Yield: 18.4 g (77% of theory), melting point: 93° C., $C_{14}H_{23}N_4O_5P$ (MW=358.34), $^1H$-NMR ($CDCl_3$) $\delta$=1.32 (t, 6H); 1.55–1.80 (m, 2H); 2.10–2.32 (m, 2H); 3.40 (s, 3H); 3.60 (s, 3H); 4.00–4.19 (m, 4H); 4.45 (t, 2H); 7.80 (s, 1H) ppm

EXAMPLE 9

Diethyl [3-(1,3-dipropylxanthin-7-yl)propyl] phosphonate

The title substance was prepared from 1,3-dipropylxanthine and diethyl 3-bromopropanephosphonate analogously to Example 1 and chromatographed on silica gel (eluent: ethyl acetate/methanol 20:1).

Yield: 6 g (49% of theory), oil, $C_{18}H_{31}N_4O_5P$ (MW=414.5), $^1H$-NMR ($CDCl_3$) $\delta$=0.94 (t, 3H); 0.97 (t, 3H); 1.30 (t, 6H); 1.55–1.76 (m, 6H); 2.08–2.30 (m, 2H); 3.91–4.28 (m, 8H); 4.40 (t, 2H); 7.61 (s, 1H) ppm

EXAMPLE 10

Diethyl [5-(1,3-dibutylxanthin-7-yl)pentyl] phosphonate

The title substance was prepared from 1,3-dibutylxanthine and diethyl 5-bromopentanephosphonate analogously to Example 9.

Yield: 2.7 g (30.2% of theory), oil, $C_{22}H_{39}N_4O_5P$ (MW= 470.6), $^1$H-NMR (CDCl$_3$) δ=0.95 (t, 3H); 0.96 (t, 3H); 1.32 (t, 6H); 1.33–1.98 (m, 16H); 3.95–4.18 (m, 8H); 4.28 (t, 2H); 7.52 (s, 1H) ppm

EXAMPLE 11

Diethyl [4-(1,3-dibutylxanthin-7-yl)butyl] phosphonate

The title substance was prepared from 1,3-dibutylxanthine and diethyl 4-chlorobutanephosphonate analogously to Example 9.

Yield: 4.5 g (52% of theory), oil, $C_{21}H_{37}N_4O_5P$ (MW= 456.5), $^1$H-NMR (CDCl$_3$) δ=0.96 (t, 3H); 0.97 (t, 3H); 1.32 (t, 6H); 1.33–2.19 (m, 14H); 3.95–4.18 (m, 8H); 4.30 (t, 2H); 7.54 (s, 1H) ppm

EXAMPLE 12

Diethyl [3-(1,3-dipropylxanthin-7-yl)propyl] phosphonate

The title substance was prepared from 1,3-dibutylxanthine and diethyl 3-bromopropanephosphonate analogously to Example 9.

Yield: 4 g (48% of theory), oil, $C_{20}H_{35}N_4O_5P$ (MW= 442.5), $^1$H-NMR (CDCl$_3$) δ=0.96 (t, 3H); 0.99 (t, 3H); 1.34 (t, 6H); 1.34–1.82 (m, 10H); 2.10–2.35 (m, 2H); 3.95–4.20 (m, 8H); 4.41 (t, 2H); 7.63 (s, 1H) ppm

EXAMPLE 13

Diethyl [4-(3-methyl-7-propylxanthin-7-yl)butyl] phosphonate

The title substance was prepared from 3-methyl-1-propylxanthine and diethyl 4-chlorobutanephosphonate analogously to Example 4 and chromatographed on silica gel (eluent: dichloromethane/methanol 10:1)

Yield: 4.5 g (47% of theory), melting point: 69° C., $C_{17}H_{29}N_4O_5P$ (MW=400.4), $^1$H-NMR (CDCl$_3$) δ=0.96 (t, 3H); 1.30 (t, 6H); 1.55–2.10 (m, 8H); 3.57 (s, 3H); 3.90–4.25 (m, 6H); 4.29 (t, 2H); 7.53 (s, 1H) ppm

EXAMPLE 14

Diethyl [4-(1-methoxyethyl-3-methylxanthin-7-yl) butyl]phosphonate

The title substance was prepared from 1-methoxyethyl-3-methylxanthine and diethyl 4-chlorobutanephosphonate analogously to Example 4 and crystallized from diisopropyl ether.

Yield: 5.6 g (37% of theory), melting point: 59° C., $C_{17}H_{29}N_4O_5P$, (MW=416.4), $^1$H-NMR (CDCl$_3$) d=1.30 (t, 6H); 1.60–2.08 (m, 6H); 3.36 (s, 3H); 3.58 (s, 3H); 3.65 (t, 2H); 4.00–4.18 (m, 4H); 4.22–4.33 (m, 4H); 7.53 (s, 1H) ppm

EXAMPLE 15

Diethyl [4-(1-(3-methylbutyl)-3-methylxanthin-7-yl) butyl]phosphonate

The title substance was prepared from diethyl [4-(3-methylxanthin-7-yl)-butyl]phosphonate and 2-methylbutyl chloride analogously to Example 1 and chromatographed on silica gel (eluent: dichloromethane/methanol 10:1)

Yield: 4.2 g (54% of theory), oil, $C_{19}H_{33}N_4O_5P$ (MW= 428.5), $^1$H-NMR (CDCl$_3$) d=0.96 (d, 6H); 1.30 (t, 6H); 1.50–2.07 (m, 9H); 3.56 (s, 3H); 3.98–4.13 (m, 6H); 4.30 (t, 2H); 7.52 (s 1H) ppm

EXAMPLE 16

Diethyl [5-(7-ethoxymethyl-3-methylxanthin-1-yl) pentyl]phosphonate a) 1-(5-Bromopentyl)-7-ethoxymethyl-3-methylxanthine 22.4 g (0.1 mol) of 7-ethoxymethylxanthine were stirred at 70° C. for 1.5 hours with 45.9 g (0.2 mol) of 1,5-dibromopentane and 27.6 g of activated potassium carbonate. The solution was filtered and concentrated, and the oily residue which remained was chromatographed (eluent: ethyl acetate).

Yield: 21.4 g (57% of theory), oil $C_{14}H_{21}BrN_4O_3$ (MW= 373.26)

2b) Diethyl [5-(7-ethoxymethyl-3-methylxanthin-1-yl) pentyl]phosphonate 4.8 g (0.035 mol) of diethyl phosphite were cooled to 0° C. in 100 ml of dry dimethylformamide and slowly treated with 0.8 g (0.035 mol) of sodium hydride. The solution was stirred at 20° C. for 0.5 hours to complete the deprotonation and then treated with 10 g (0.0268 mol) of 1-(5-bromopentyl)-7-ethoxymethyl-3-methylxanthine, dissolved in a little dimethyl-formamide. After 4 hours at 20° C., the reaction mixture was quenched with a little saturated ammonium chloride solution, concentrated and chromatographed on silica gel (eluent: dichloromethane/methanol 15:1).

Yield: 5.1 g (44% of theory), oil, $C_{18}H_{31}N_4O_6P$ (MW= 430.4), $^1$H-NMR (CDCl$_3$) d=1.20 (t, 3H); 1.30 (t, 6H); 1.36–1.82 (m, 8H); 3.59 (s, 3H); 3.62 (q, 2H); 3.95–4.18 (m, 6H); 5.70 (s, 2H); 7.74 (s, 1H) ppm

EXAMPLE 17

Diethyl [5-(3-methyl-7-propylxanthin-1-yl)-pentyl] phosphonate

The title substance was prepared from 1-(5-bromopentyl) -3-methyl-7-propylxanthine and diethyl phosphite analogously to Example 16.

Yield: 10 g (29% of theory), oil, $C_{18}H_{31}N_4O_5P$ (MW= 414.5), $^1$H-NMR (CDCl$_3$) δ=0.94 (t, 3H); 1.29 (t, 6H); 1.40–1.95 (m, 10H); 3.56 (s, 3H); 3.95–4.15 (m, 6H); 4.23 (t, 2H); 7.52 (s, H) ppm

EXAMPLE 18

Diethyl [5-(7-methoxyethyl-3-methylxanthin-1-yl) pentyl]phosphonate a) Diethyl 5-p-toluenesulfonyloxypentylphosphonate 30 g (0.134 mol) of diethyl 5-hydroxypentylphosphonate (see Example 21) were dissolved in 200 ml of pyridine, and the solution was cooled to 0° C. and treated with stirring with 26.1 g (0.134 mol) of 4-toluenesulfonyl chloride. The reaction mixture was concentrated under reduced pressure, taken up in ethyl acetate, washed several times with 20% strength citric acid solution and water and dried over sodium sulfate. After evaporating the solvent, a pale yellow oil remained, which was employed without further purification.

Yield: 37.5 g (74% of theory), b) Diethyl [5-(7-methoxyethyl-3-methylxanthin-1-yl) pentyl]phosphonate 9.3 g (0.0245 mol) of the sulfonic acid ester of a) were stirred at 80° C. for 8 hours with 5.5 g (:0.0245 mol) of 7-methoxyethylxanthine and 6.7 g (0.049 mol) of activated potassium carbonate in 150 ml of dimethylformamide. The reaction solution was then filtered and concentrated, and the residue was chromatographed on silica gel (eluent: ethyl acetate/methanol 20:1). After concentrating the corresponding solution, a pale yellow oil remained.

Yield: 6.2 g (59% of theory), $C_{18}H_{31}O_6P$ (MW=430.4), $^1$H-NMR (CDCl$_3$) δ=1.30 (t, 6H); 1.40–1.85 (m, 8H); 3.32 (s, 3H); 3.57 (s, 3H); 3.69 (t, 2H); 4.05 (m, 6H); 4.45 (t, 2H); 7.62 (s, 1H) ppm

EXAMPLE 19

Diethyl 5-(3,7-dimethylxanthin-1-yl) pentylphosphonate

The title substance was prepared from 0.0245 mol of diethyl 5-p-toluene-sulfonyloxypentylphosphonate and 0.02 mol of 1,7-dimethylxanthine analogously to Example 18 and chromatographed on silica gel (eluent: ethyl acetate/methanol 10:1).

Yield: 3.1 g (30% of theory), melting point: 85° C., $C_{16}H_{27}N_4O_5P$ (MW=386.4), $^1$H-NMR (CDCl$_3$) δ=1.30 (t, 6H); 1.35–1.88 (m, 8H); 3.55 (s, 3H); 3.97 (s, 3H); 3.95–4.15 (m, 6H); 7.50 (s 1H) ppm

EXAMPLE 20

Diethyl 5-(7-ethyl-3-methylxanthin-1-yl) pentylphosphonate

The title substance was prepared from 0.0245 mol of ethyl 5-p-toluene-sulfonyloxypentylphosphonate and 0.024 mol of 7-ethyl-3-methylxanthine analogously to Example 19.

Yield: 6.9 g (70% of theory), melting point: 61°–63° C., $C_{17}H_{29}N_4O_5P$ (MW=400.4), $^1$H-NMR (CDCl$_3$) δ=1.30 (t, 6H); 1.51 (t, 3H); 1.51–1.82 (m,8H); 3.57 (s 3H); 3.95–4.18 (m, 6H); 4.33 (q, 2H); 7.55 (s, 1H) ppm

EXAMPLE 21

Diethyl 5-(7-ethoxymethyl-3-methylxanthin-1-yl)-1,1-dimethylpentyl-phosphonate a) 5-(Diethylphosphono)pentyl acetate 100.34 g (0.48 mol) of 5-bromopentyl acetate were heated at 150° C. for 8 hours with 79.8 g (0.048 mol) of triethyl phosphite while stirring and passing in nitrogen. The mixture was then fractionally distilled under reduced pressure.

Yield: 92 g (72% of theory), boiling point (0.4 mbar) 132°–135° C., $C_{11}H_{23}O_5P$ (MW=266.3)

b) Diethyl 5-hydroxypentylphosphonate 92 g (0.345 mol) of 5-(diethylphosphono)pentyl acetate were heated at 50° C. for 10 hours with stirring with 74 g (0.7 mol) of finely powdered sodium carbonate in 500 ml of methanol. The solution was filtered, concentrated and distilled in a bulb tube.

Yield: 66.9 g (86.5% of theory), boiling point (0.1 mbar) 110°–130° C., $C_9H_{21}O_4P$ (MW=224.2), $^1$H-NMR (CDCl$_3$) δ=1.31 (t, 6H); 1.38°–1.80 (m, 8H); 1.90 (s, 1H); 3.63 (t, 2H); 4.08 (m, 4H) ppm c) Diethyl 5-(tetrahydropyran-2-yloxy) pentylphosphonate A solution of 66.9 g (0.298 mol) of diethyl 5-hydroxypentylphosphonate, 32.6 g (0.38 mol) of 3,4-dihydropyran and 1 g (0.004 mol) of pyridinium toluene-4-sulfonate in 800 ml of dichloromethane was heated under reflux for 16 hours. The solution was washed with water and saturated sodium hydrogen carbonate solution, dried over sodium sulfate and distilled in a bulb tube.

Yield: 89.5 g (97.4% of theory), boiling point (0.1 mbar) 110°–130° C., $C_{14}H_{29}O_5P$ (MW=308.3), $^1$H-NMR (CDCl$_3$) δ=1.31 (t, 6H); 1.39–1.82 (m, 14H); 3.42 (m, 2H); 3.75 (m, 2H); 4.08 (m, 4H); 4.65 (m, 1H) ppm d) Diethyl 1-methyl-5-(tetrahydropyran-2-yloxy) pentylphosphonate 30 g (0.097 mol) of diethyl 5-(tetrahydropyran-2-yloxy) pentylphosphonate were initially introduced into 200 ml of absolute tetrahydrofuran under an argon atmosphere, cooled to −70° C. and treated with 42.8 ml (0.107 mol) of a 2.5 molar solution of butyllithium in hexane. After addition, the solution was stirred for a further 30 minutes and 15.6 g (0.11 mol) of methyl iodide were then slowly added dropwise. The mixture was stirred at −70° C. for a further 2 hours and at room temperature for 4 hours, cautiously treated with a saturated sodium chloride solution and taken up in ethyl acetate. The organic phase was washed with water and a saturated sodium chloride solution, dried over sodium sulfate and distilled in a bulb tube.

Yield: 23.4 g (75% of theory), boiling point (0.1 mbar) 120° C., $C_{15}H_{31}O_5P$ (MW=322.4), $^1$H-NMR (CDCl$_3$) δ=1.10 (d, 1.5H); 1.19 (d, 1.5H); 1.31 (t, 6H); 1.30–1.89 (m, 13H); 3.42 (m, 2H); 3.78 (m, 2H); 4.08 (m, 4H), 4.55 (m, 1H) ppm e) Diethyl 1,1-dimethyl-5-(tetrahydropyran-2-yloxy)-5-pentylphosphonate 23.3 g (0.0724 mol) of diethyl 1-methyl-5-(tetranydropyran-2-yloxy)pentylphosphonate were initially introduced into 200 ml of absolute tetrahydrofuran under an argon atmosphere, cooled to −70° C. and treated with 31.9 ml (0.08 mol) of a 2.5 molar solution of butyllithium in hexane. After addition was complete, the solution was stirred for a further 30 minutes and 12.3 g (0.087 mol) of methyl iodide were then slowly added dropwise. The mixture was stirred at −70° C. for a further 2 hours and at room temperature for 4 hours, cautiously treated with a saturated sodium chloride solution and taken up in ethyl acetate. The organic phase was washed with water and a saturated sodium chloride solution, dried over Sodium sulfate and distilled in a bulb tube.

Yield: 19.9 g (75% of theory), boiling pint (0.1 mbar) 115°–125° C., $C_{16}H_{33}O_5P$ (MW=336.4), $^1$H-NMR (CDCl$_3$) δ=1.09 (s, 3H); 1.17 (s, 3H); 1.30 (t, 6H); 1.38–1.89 (m, 12H); 3.44 (m, 2H); 3.74 (m, 2H); 4.09 (m, 4H), 4.56 (m, 1H) ppm f) Diethyl 5-hydroxy-1,1-dimethylpentylphosphonate 19.9 g (0.052 mol) of diethyl 1,1-dimethyl-5-(tetrahydropyran-2-yloxy)-5-pentylphosphonate were stirred at 55° C. for 8 hours with 1.5 g (0.006 mol) of pyridinium toluene-4-sulfonate in 200 ml of aqueous ethanol. The solvent was evaporated, the residue was taken up in ethyl acetate, the solution was filtered through a silica gel column and, after evaporating the solvent, the residue was distilled in a bulb tube.

Yield: 12.8 g (86.7% of theory), boiling point (0.1 mbar) 120°–130° C., $C_{11}H_{25}O_4P$ (MW=252.3)

g) Diethyl 5-p-toluenesulfonoxy-1,1-dimethylpentylphosphonate 12.8 g (0.051 mol) of diethyl 5-hydroxy-1,1-dimethylpentylphosphonate were dissolved in 100 ml of pyridine, cooled to 0° C. and slowly treated with 9.7 g (0.051 mol) of 4-toluenesulfonyl chloride. The reaction mixture was concentrated under reduced pressure, the residue was taken up in ethyl acetate, and the solution was washed several times with 20% strength citric acid solution and water and dried over sodium sulfate. After evaporating the solvent, a pale yellow oil (17.2 g) remained, which was employed without further purification.

Yield: 6.74 g (32.5% of theory)

h) Diethyl 5-(7-ethoxymethyl-3-methylxanthin-1-yl)-1,1-dimethylpentyl-phosphonate 6.75 g (0.017 mol) of the sulfonic acid ester of g) were stirred at 80° C. for 8 hours with 3.73 g (0.017 mol) of 7-ethoxymethylxanthine and 4.6 g (0.033 mol) of activated potassium carbonate in 100 ml of dimethylformamide. The reaction solution was then filtered, concentrated and chromatographed on silica gel (eluent: ethyl acetate/methanol 20:1). After concentrating the resulting fractions a pale yellow oil remained.

Yield: 4 g (44% of theory), $C_{20}H_{35}N_4O_6P$ (MW=458.5), $^1$H-NMR (CDCl$_3$) δ=1.14 (d, 6H); 1.23 (t, 3H); 1.30 (t, 6H); 1.35–1.73 (m, 6H); 3.59 (s, 3H); 3.63 (q, 2H); 4.07 (m, 4H); 5.70 (s, 2H); 7.74 (s, 1H) ppm

EXAMPLE 22

Diethyl [5-(7-methoxyethyl-3-methylxanthin-1-yl)-1,1-dimethylpentyl]-phosphonate The title substance was prepared from 0.02 mol of the sulfonic acid ester and 0.02 mol of 7-methoxyethyl-3-methylxanthine analogously to Example 2.

Yield: 3.8 g (39% of theory), $C_{20}H_{35}N_4O_6P$ (MW=458.5), $^1$H-NMR (CDCl$_3$) δ=1.13 (d, 6H); 1.30 (t, 6H); 1.35–1.70 (m, 6H); 3.31 (s, 3H); 3.57 (s, 3H); 3.70 (t, 2H); 3.95–4.18 (m, 6H); 4.47 (t, 2H); 7.62 (s, 1H) ppm

EXAMPLE 23

Diethyl [4-(7-benzyl-3-methylxanthin-1-yl)butyl] phosphonate 20.4 g (0.08 mol) of 7-benzyl-3-methylxanthine were suspended in 200 ml of dimethylformamide (DMF), treated with 22 g (0.96 mol) of diethyl 4-chlorobutanephosphonate and 13.8 g (0.1 mol) of activated potassium carbonate and heated at 70° C. for 4 hours and filtered, the filtrate was concentrated under reduced pressure and the oily residue which remained was taken up in ethyl acetate, filtered again and crystallized from diisopropyl ether.

Yield: 22.6 g (63% of theory), melting point: 120°–121° C., $C_{21}H_{29}N_4O_5P$ (MW=448.5), $^1$H-NMR (CDCl$_3$) δ=1.23 (t, 6H); 1.70 (m, 6H); 3.55 (s, H); 4.07 (m, 6H); 5.48 (s, 2H); 7.33 (m, 5H); 7.54 (s, 1H) ppm

EXAMPLE 24

Diethyl [4-(3-methylxanthin-1-yl)-butyl] phosphonate 15.7 g (0.035 mol) of diethyl [4-(7-benzyl-3-methylxanthin-1-yl)butyl]-phosphonate were hydrogenated in 150 ml of ethanol over 1 g of palladium (10%) on active carbon at room temperature in the course of 8 hours. The catalyst was filtered off, the filtrate was concentrated under reduced pressure and the residue was crystallized from diisopropyl ether.

Yield: 11.7 g (93% of theory), melting point: 140°–141° C., $C_{14}H_{23}N_4O_5P$ (MW=358.3), $^1$H-NMR (CDCl$_3$) δ=1.34 (t, 6H); 1.60–2.15 (m, 6H); 3.64 (s, 3H); 4.10 (m, 6H); 7.85 (s, 1H); 11.2 (s, 1H) ppm

EXAMPLE 25

Diammonium [4-(3-methylxanthin-1-yl)butyl] phosphonate 5.2 g (0.0125 mol) of diethyl [4-(3-methylxanthin-1-yl)butyl]phosphonate were heated under reflux with 30 ml of 20% strength hydrochloric acid for 4 hours. The hydrochloric acid was evaporated and the oily residue was dried over potassium hydroxide in a desiccator. The phosphonic acid formed was then treated with a methanolic ammonia solution, the solvent was evaporated and the residue was crystallized from a methanol/diisopropyl ether mixture.

Yield: 3.6 g (85.6% of theory), melting point: >220° C., $C_{10}H_{21}N_6O_5P$ (MW=336.3), $^1$H-NMR (D$_2$O) δ=1.45–1.70 (m, 6H); 343 (s, 3H); 3.85 (t, 2H); 7.92 (s, 1H) ppm

EXAMPLE 26

Diethyl [4-(7-ethoxymethyl-3-methylxanthin-1-yl) butyl]phosphonate 44.8 g (0.2 mol) of 7-ethoxymethyl-3-methylxanthine were suspended in 500 ml of DMF, treated with 55 g (0.24 mol) of diethyl 4-chlorobutane-phosphonate and 50 g (0.32 mol) of activated potassium carbonate and heated at 70° C. for 4 hours and filtered, the filtrate was concentrated under reduced pressure and the oily residue which remained was taken up in ethyl acetate, filtered again and crystallized from diisopropyl ether.

Yield: 68.3 g (82% of theory), melting point: 109°–110° C., $C_{17}H_{29}N_4O_6P$ (MW=416.4), $^1$H-NMR (CDCl$_3$) δ=1.20 (t, 3H); 1.31 (t, 6H); 1.60–1.90 (m, 6H); 3.59 (s, 3H); 3.63 (q, 2H); 3.95–4.18 (m, 6H); 5.70 (s, 2H); 7.74 (s, 1H)

EXAMPLE 27

Ammonium [4-(7-ethoxymethyl-3-methylxanthin-1-yl)-butyl]phosphonate a) Ethyl 4-chlorobutanechlorophosphonate 14 g (0.062 mol) of diethyl 4-chlorobutanephosphonate in 150 ml of absolute carbon tetrachloride were treated in portions with 12.8 g (0.062 mol) of phosphorus pentachloride with stirring and cooling to 20° C. in the course of 4 hours. After further stirring at room temperature, fractional distillation yielded 8.45 g (0.039 mol) of the corresponding acid chloride.

Yield: 8.45 g (60% of theory), boiling point (0.2 mbar): 102°–108° C., $C_6H_{13}ClO_2P$ (MW=219.1)

b) 1-Benzylethyl 4-chlorobutanechlorophosphonate 8.4 g (0.038 mol) of ethyl 4-chlorobutanechlorophosphonate were dissolved in 100 ml of dichloromethane, treated with 4.01 g (0.04 mol) of triethylamine and cooled to 0° C. 5.4 g (0.05 mol) of benzyl alcohol were then added and the reaction mixture was stirred at 0° C. for 1 hour and at room temperature for 4 hours. The solution was washed with water, 20% strength citric acid and saturated sodium hydrogen carbonate, dried over sodium sulfate and, after evaporating the dichloromethane, distilled in a bulb tube.

Yield: 8.3 g (72% of theory), boiling point (0.1 mbar) >90° C., $C_{13}H_{20}ClO_3P$ (MW=290.7)

c) Benzylethyl [4-(7-ethoxymethyl-3-methylxanthin-1-yl)butyl]phosphonate 6 g (0.027 mol) of 7-ethoxymethyl-3-methylxanthine were suspended in 70 ml of DMF, treated with 7.85 g (0.027 mol) of 1-benzylethyl 4-chlorobutanephosphonate and 5 g (0.032 mol) of activated potassium carbonate and heated at 70° C. for 4 hours and filtered, the filtrate was concentrated under reduced pressure and the oily residue which remained was chromatographed on a silica gel column (eluent: dichloromethane/methanol 15:1).

Yield: 6.5 g (50.3% of theory), oil, $C_{22}H_{31}N_4O_6P$ (MW=478.5), $^1$H-NMR (CDCl$_3$) δ=1.12 (t, 3H); 1.26 (t, 3H); 1.50–1.90 (m, 6H); 3.59 (s,3H); 3.62 (q, 2H); 3.95–4.18 (m, 6H); 5.02 (s, 1H); 5.06 (s, 1H); 5.69 (s, 2H); 7.15–7.43 (m, 5H); 7.87 (s, 1H) ppm d) Monoethyl ammonium [4-(7-ethoxymethyl-3-methylxanthin-1-yl)butyl]-phosphonate 6.3 g (0.013 mol) of benzylethyl 4-(7-ethoxymethyl-3-methylxanthin-1-yl)-butylphosphonate were hydrogenated in 100 ml of ethanol over 0.5 g of palladium (10%) on active carbon at room temperature in the course of 4 hours. The catalyst was filtered off, the filtrate was concentrated under reduced pressure, the solution obtained was treated with methanolic ammonia and the residue which remained after evaporating the solvent was then crystallized from diisopropyl ether.

Yield: 4.6 g (87% of theory), melting range: 84°–96° C., $C_{15}H_{28}N_5O_6P$ (MW=405.4), $^1$H-NMR (DMSO-d$_6$) δ=1.09 (t, 3H); 1.10 (t, 3H); 1.20–1.60 (m, 6H); 3.43 (s, 3H); 3.52 (q, 2H); 3.59–3.78 (m, 2H); 3.85 (t, 2H); 5.62 (s, 2H); 7.62 (s, 4H, NH$_4$); 8.28 (s, 1H) ppm

EXAMPLE 28

Diammonium [4-(7-ethoxymethyl-3-methylxanthin-1-yl)butyl]phosphonate 3.4 ml (0.026 mol) of trimethylsilyl bromide were slowly added dropwise at 0° C., under an argon atmosphere, to a solution of 4.16 g (0.01 mol) of [4-(7-ethoxymethyl-3-methylxanthin-1-yl)butyl]phosphonate in 5 ml of dichloromethane. The solution was stirred at 0° C. for 1 hour and at room temperature for 2 hours. The dichloromethane was then evaporated and the oily residue which remained was dried in a bulb tube in an oil pump vacuum to remove excess trimethylsilyl bromide and ethyl bromide formed. The residue was taken up in a little methanol and treated with 1 ml of concentrated ammonia solution and stirred at room temperature for 2 hours. After evaporating the solvent, the diammonium salt was crystallized from a methanol‌diisopropyl ether mixture.

Yield: 2.96 g (75% of theory), melting point: 159° C., $C_{13}H_{21}N_4O_6P$ (MW=360.3). $^1$H-NMR (D$_2$O) δ=1.11 (t, 3H); 1.40–1.75 (m, 6H); 3.47 (s, 3H); 3.60 (q, 2H); 3.90 (t, 2H); 5.64 (s, 2H); 8.12 (s, 1H) ppm

EXAMPLE 29

Diethyl [4-(3,7-dimethylxanthin-1-yl)-butyl] phosphonate

The title substance was prepared from 0.075 mol of theobromine and 0.09 mol of diethyl 4-chlorobutanephosphonate analogously to Example 23 and crystallized from diisopropyl ether.

Yield: 6.1 g (22% of theory), melting point: 80° C., $C_{15}H_{25}N_4O_5P$ (MW=372.4), $^1$H-NMR (CDCl$_3$) δ=1.31 (t, 6H); 1.62–1.90 (m, 6H); 3.56 (s 3H); 3.98 (s, 3H); 3.98–4.18 (m, 6H); 7.50 (s, 1H) ppm

EXAMPLE 30

Diethyl [4-(7-ethyl-3-methylxanthin-1-yl)butyl] phosphonate 7.2 g (0.02 mol) of diethyl [4-(3-methylxanthin-1-yl)-butyl]phosphonate were suspended in 100 ml of DMF, treated with 4.7 g (0.03 mol) of ethyl iodide and 4.1 g (0.03 mol) of activated potassium carbonate and heated at 60° C. for 4 hours. The solid was filtered off, the filtrate was concentrated under reduced pressure and the oily residue which remained was taken up in ethyl acetate, filtered again and crystallized from diisopropyl ether.

Yield: 4.9 g (63% of theory), melting point: 62°–63° C., $C_{16}H_{27}N_4O_5P$ (MW=386.4), $^1$H-NMR (CDCl$_3$) d=1.31 (t, 6H); 1.51 (t, 3H); 1.35–1.85 (m, H); 3.57 (s, 3H); 3.94–4.20 (m, 6H); 4.33 (q, 2H); 7.55 (s, 1H) ppm

EXAMPLE 31

Diethyl [4-(7-methoxyethyl-3-methylxanthin-1-yl) butyl]phosphonate 9 g (0.04 mol) of 7-methoxyethyl-3-methylxanthine were suspended in 100 ml of DMF, treated with 11 g (0.048 mol) of diethyl 4-chlorobutane-phosphonate and 10 g (0.064 mol) of activated potassium carbonate and heated at 70° C. for 4 hours. The solid was filtered off, the filtrate was concentrated under reduced pressure and the oily residue which remained was taken up in ethyl acetate, filtered again and crystallized from diisopropyl ether.

Yield: 12.1 g (72% of theory), melting point: 126°–127° C., $C_{17}H_{29}N_4O_6P$ (MW=416.4), $^1$H-NMR (CDCl$_3$) δ=1.31 (t, 6H); 1.45–1.70 (m, 6H); 3.32 (s, 3H); 3.56 (s, 3H); 3.69 (t, 2H); 3.95–4.15 (m, 6H); 4.47 (t, 2H); 7.63 (s, 1H)

EXAMPLE 32

Diethyl [4-(3-methyl-7-propyl-xanthin-1-yl)butyl] phosphonate

The title substance was prepared from 0.072 mol of 3-methyl-7-propyl-xanthine and 0.072 mol of diethyl 4-chlorobutanephosphonate analogously to Example 23, chromatographed on silica gel (eluent: dichloromethane/methanol 20:1) and crystallized from diisopropyl ether.

Yield: 14.4 g (50% of theory), melting point: 88°–90° C., $C_{17}H_{29}N_4O_5P$ (MW=400.4), $^1$H-NMR (CDCl$_3$) d=0.94 (t, 3H); 1.30 (t, 6H); 1.56–1.98 (m, 8H); 3.56 (s, 3H); 3.95–4.15 (m, 6H); 4.22 (t, 2H); 7.52 (s, 1H) ppm

EXAMPLE 33

Diethyl [3-(3,7-dimethylxanthin-1-yl)propyl] phosphonate

The title substance was prepared from 0.067 mol of theobromine and 0.08 mol of diethyl 3-bromopropanephosphonate analogously to Example 32.

Yield: 15.6 g (65% of theory), melting point: 50°–56° C., $C_{14}H_{23}N_4O_5P$ (MW=358.3), $^1$H-NMR (CDCl$_3$) δ=1.30 (t, 6H); 1.70–2.10 (m, 4H); 3.59 (s, 3H); 4.00 (s, 3H); 4.05–4.18 (m, 6H); 7.73 (s, 1H) ppm

EXAMPLE 34

Diethyl [3-(7-ethyl-3-methylxanthin-1-yl)propyl] phosphonate

The title substance was prepared from 0.041 mol of 7-ethyl-3-methyl-xanthine and 0.049 mol of diethyl 3-bromopropanephosphonate analogously to Example 32.

Yield: 12.3 g (80% of theory), melting point: 108° C., $C_{15}H_{25}N_4O_5P$ (MW=372.4), $^1$H-NMR (CDCl$_3$) δ=1.31 (t, 6H); 1.53 (t, 3H); 1.70–2.10 (m, 4H); 3.59 (s, 3H); 4.12–4.18 (m, 6H); 4.36 (q, 2H); 7.62 (s, 1H) ppm

EXAMPLE 35

Diethyl [3-(7-methoxyethyl-3-methylxanthin-1-yl)propyl]phosphonate

The title substance was prepared from 0.048 mol of 7-methoxymethyl-3-methylxanthine and 0.058 mol of diethyl 3-bromopropanephosphonate analogously to Example 32.

Yield: 8.6 g (45% of theory), oil, $C_{16}H_{27}N_4O_5P$ (MW=402.4), $^1$H-NMR (CDCl$_3$) δ=1.29 (t, 6H); 1.70–2.05 (m, 4H); 3.30 (s, 3H); 3.56 (s, 3H); 3.68 (t, 2H); 3.95–4.15 (m, 6H); 4.45 (t, 2H); 7.61 (s, 1H) ppm

EXAMPLE 36

Diethyl [3-(7-ethoxymethyl-3-methylxanthin-1-yl)propyl]phosphonate

The title substance was prepared from 0.048 mol of 7-ethoxymethyl-3-methylxanthine and 0.058 mol of diethyl 3-bromopropanephosphonate analogously to Example 32 and chromatographed on silica gel (eluent: ethyl acetate/methanol 10:1).

Yield: 8.5 g (44% of theory), oil, $C_{16}H_{27}N_4O_5P$ (MW=402.4), $^1$H-NMR (CDCl$_3$) δ=1.17 (t, 3H); 1.28 (t, 6H); 1.70–2.05 (m, 4H); 3.56 (s, 3H); 3.59 (q, 2H); 3.95–4.15 (m, 6H); 5.68 (s, 2H); 7.73 (s, 1H) ppm

EXAMPLE 37

Diethyl [4-(3-ethylxanthin-1-yl)butyl]phosphonate a) 7-Benzyl-3-ethylxanthine 18 g (0.1 mol) of 3-ethylxanthine were stirred at 60° C. for 2 hours with 19.2 g (0.11 mol) of benzyl bromide and 15.2 g (0.11 mol) of potassium carbonate. The reaction solution was transferred to an Edenmeyer flask and treated with 1000 ml of water. The precipitate was filtered off with suction, washed several times with warm water and dried at 50° C. under reduced pressure.

Yield: 24.3 g (90% of theory), $C_{14}H_{14}N_4O_2$ (MW=270.3)

b) Diethyl [4-(7-benzyl-3-ethylxanthin-1-yl)butyl]phosphonate

The title substance was prepared from 0.04 mol of 7-benzyl-3-ethyl-xanthine and 0.048 mol of diethyl 4-chlorobutanephosphonate analogously to Example 23.

Yield: 15.8 g (85% of theory), $C_{22}H_{31}N_4O_5P$ (MW=462.5)

c) Diethyl [4-(3-ethylxanthin-1-yl)butyl]phosphonate

The title substance was prepared from 0.03 mol of diethyl [4-(7-benzyl-3-ethylxanthin-1-yl)butyl]phosphonate analogously to Example 23.

Yield: 10.5 g (93% of theory), melting point: 134° C., $C_{15}H_{25}N_4O_5P$ (MW=372.4), $^1$H-NMR (CDCl$_3$) δ=1.23–1.40 (m, 9H); 1.60–1.95 (m, 6H); 3.98–4.25 (m, 8H); 7.82 (s 1H); 13.10 (s, 1H, NH) ppm

EXAMPLE 38

Diethyl [4-(3-ethyl-7-propylxanthin-1-yl)butyl]phosphonate

The title substance was prepared from 8.2 mmol of diethyl [4-(3-ethyl-xanthin-1-yl)butyl]phosphonate and 9.8 mmol of bromopropane analogously to Example 30 and chromatographed on silica gel (eluent: dichloromethane/methanol 20:1).

Yield: 2.7 g (80% of theory), melting point: 102° C., $C_{18}H_{31}N_4O_5P$ (MW=414.45), $^1$H-NMR (CDCl$_3$) δ=0.95 (t, 3H); 1.30 (t, 6H); 1.33 (t, 3H); 1.55–1.98 (m, 8H); 3.95–4.28 (m, 10H); 7.52 (s, 1H) ppm

EXAMPLE 39

Diethyl [3-(3-cyclopropyl-7-propylxanthin-1-yl)butyl]phosphonate a) Cyclopropylurea 400.5 g (6.87 mol) of cyclopropylamine were treated with 1400 ml of 5N hydrochloric acid with ice-cooling and then with 568 g (6.87 mol) of potassium cyanate. The solution was stirred at 70° C. for a further 4 hours, evaporated to dryness in a water-jet vacuum and the residue was taken up in 2000 ml of ethanol. The precipitated potassium chloride was filtered off, the filtrate was concentrated and the residue was treated with petroleum ether. The crystalline precipitate was filtered off with suction, washed with petroleum ether and dried in air.

Yield: 659.7 g (95% of theory, possibly contaminated with potassium chloride), melting point: 100°–120° C., $C_4H_8N_2O$ (MW=100)

b) 1-Cyanoacetyl-3-cyclopropylurea 450 g (3.875 mol) of cyclopropylurea were slowly introduced at a temperature of 80° C. into a solution of 329 g (3.875 mol) of cyanoacetic acid in 476 g (4.57 mol) of acetic anhydride. The solution was heated to 90° C. and stirred at this temperature for 2 hours. It was then cooled to 20° C., and the precipitate was filtered off with suction, washed with water and dried to constant weight at 80° C.

Yield: 503 g (78% of theory), melting point: 179° C., $C_7H_9N_3O_2$ (MW=167.1)

c) 1-Cyclopropyl-6-aminouracil

The cyclization of 1-cyanoacetyl-3-cyclopropylurea (3 mol) was carried out analogously to the known processes.

Yield: 317 g (63% of theory), melting point: 278° C., $C_7H_9N_3O_2$ (MW=167.1)

d) 3-Cyclopropylxanthine

The preparation of 3-cyclopropylxanthine from 1-cyclopropyl-6-aminouracil (1.88 mol) was carried out analogously to the known processes.

Yield: 174.6 g (48% of theory), melting point: 294° C. (decomp.), $C_8H_8N_4O_2$ (MW=192.2)

e) 3-Cyclopropyl-7-propylxanthine 9.6 g (0.05 mol) of 3-cyclopropylxanthine were suspended in 150 ml of dimethylformamide and slowly deprotonated using 1.45 g (0.06 mol) of sodium hydride. When evolution of hydrogen was at an end, the solution was heated to 60° C. and treated dropwise with 6.77 g (0.055 mol) of bromopropane. After stirring at 70° C. for 3 hours, the solution was filtered, the dimethylformamide was evaporated under reduced pressure and the residue was crystallized from diisopropyl ether.

Yield: 7.5 g (64% of theory), melting point: 163° C., $C_{11}H_{14}N_4O_2$ (MW=234.3), $^1$H-NMR (CDCl$_3$) δ=0.94 (t, 3H); 1.00–1.25 (m, 4H); 1.80–2.00 (m, 2H); 2.89–3.02 (m, 1H); 4.22 (t, 2H); 7.56 (s, 1H); 8.45 (s, 1H, NH) ppm f) Diethyl [3-(3-cyclopropyl-7-propylxanthin-1-yl)butyl]phosphonate 3-Cyclopropyl-7-propylxanthine (0.015 mol) was alkylated as in Example 4. The solution was filtered and concentrated, and the residue which remained was chromatographed (eluent: dichloromethane/methanol 15:1).

Yield: 3.8 g (62% of theory), oil, $C_{18}H_{29}N_4O_5P$ (MW=412.4), $^1$H-NMR (CDCl$_3$) δ=0.93 (t, 3H); 0.95–1.20 (m, 4H); 1.29 (t, 6H); 1.70–2.05 (m, 6H); 2.92–3.05 (m, 1H); 3.95–4.13 (m, 6H); 4.21 (t, 2H); 7.53 (s, 1H); (H) ppm

EXAMPLE 40

Diethyl [3-(3,7-dibutylxanthin-1-yl)propyl] phosphonate

The title substance was prepared from 0.02 mol of 3,7-dibutylxanthine and 0.022 mol of diethyl 3-bromopropanephosphonate analogously to Example 23 and chromatographed on silica gel (eluent: dichloromethane/methanol 20:1).

Yield: 4.5 g (54% of theory), oil, $C_{20}H_{35}N_4O_5P$ (MW=442.5), $^1$H-NMR (CDCl$_3$) δ=0.93 (t, 6H); 1.20–1.45 (m, 10H); 1.63–2.05 (m, 8H); 3.95–4.16 (m, 8H); 4.23 (t, 2H); 7.50 (s, 1H) ppm

EXAMPLE 41

Diethyl {4-[7-(3-methylbutyl)-3-methylxanthin-1-yl)butyl]phosphonate a) 7-(3-Methylbutyl)-3-methylxanthine 100 g (0.602 mol) of 3-methylxanthine, dissolved in 1200 ml of DMF, were slowly treated with 16 g (0.66 mol) of sodium hydride. The solution was heated to 60° C. and, when the evolution of hydrogen was at an end, treated with 109 g (0.66 mol) of 1-bromo-3-methylbutane. The reaction mixture was stirred at 100° C. for 12 hours and introduced into 2000 ml of water. The precipitate was filtered off with suction, washed with water and dried to constant weight.

Yield: 113.5 g (80% of theory), melting point: 204° C., $C_{11}H_{16}N_4O_2$ (MW=236.3)

b) Diethyl {4-[7-(3-methylbutyl)-3-methylxanthinyl-yl)butyl]phosphonate

The title substance was prepared from 0.0254 mol of 7-(3-methylbutyl)-3-methylxanthine and 0.03 mol of diethyl 4-chlorobutanephosphonate analogously to Example 23 and chromatographed on silica gel (eluent: dichloromethane/methanol 20:1) and crystallized from diisopropyl ether.

Yield: 2.2 g (20% of theory), melting point: 118° C., $C_{19}H_{33}N_4O_5P$ (MW=428.5), $^1$H-NMR (CDCl$_3$) δ=0.96 (d, 6H); 1.31 (t, 6H); 1.54–1.90 (m, 9H); 3.56 (s, 3H); 3.95–4.18 (m, 6H); 4.30 (t, 2H); 7.52 (s, 1H) ppm

EXAMPLE 42

Diethyl [3-(3-methylxanthin-1-yl)propyl] phosphonate a) Diethyl [7-benzyl-3-(3-methylxanthin-1-yl)propyl] phosphonate The title substance was prepared from 7-benzyl-3-methylxanthine, (0.04 mol) and diethyl 3-bromopropanphosphonate (0.046 mol) analogously to Example 23.

Yield: 12 g (70% of theory), oil, $C_{20}H_{27}N_4O_5P$ (MW=434.5)

b) Diethyl [3-(3-methylxanthin-1-yl)propyl]phosphonate

The title substance was prepared from 0.026 mol of diethyl [7-benzyl-3-(3-methylxanthin-1-yl)propyl] phosphonate analogously to Example 24 and crystallized from diisopropyl ether.

Yield: 8.6 g (89% of theory), melting point: 125° C., $C_{13}H_{21}N_4O_5P$ (MW=344.3), $^1$H-NMR (CDCl$_3$) δ=1.31 (t, 6H); 1.78–2.14 (m, 4H); 3.62 (s, 3H); 4.00–4.19 (m, 6H); 7.83 (s, 1H); 13.02 (s, 1H, NH) ppm

EXAMPLE 43

Diethyl [5-(7-benzyl-3-methylxanthin-1-yl)pentyl] phosphonate

The title compound was prepared from 7-benzyl-3-methylxanthine (0.059 mol) and diethyl 5-bromopentanephosphonate (0.07 mol) analogously to Example 23.

Yield: 21.8 g (80% of theory), oil, $C_{22}H_{31}N_4O_5P$ (MW=462.5), $^1$H-NMR (CDCl$_3$) δ=1.30 (t, 6H); 1.40–1.82 (m, 8H); 3.56 (s, 3H); 3.95–4.15 (m, 6H); 5.48 (s, 2H); 7.32–7.36 (m, 5H); 7.54 (s, 1H) ppm

EXAMPLE 44

Diethyl [3-(3-methylxanthin-1-yl)pentyl] phosphonate

The title substance was prepared from 0.045 mol of diethyl [7-benzyl-3-(3-methylxanthin-1-yl)pentyl] phosphonate analogously to Example 24 and crystallized from ethyl acetate/diisopropyl ether.

Yield: 11.7 g (70% of theory), melting point: 109° C., $C_{15}H_{25}N_4O_5P$ (MW=372.4), $^1$H-NMR (CDCl$_3$) δ=1.31 (t, 6H); 1.38–1.88 (m, 8H); 3.63 (s, 3H); 4.00–4.18 (m, 6H); 7.82 (s, 1H); 12.98 (s, 1H, NH) ppm

EXAMPLE 45

Diethyl [4-(3-ethyl-7-methoxyethylxanthin-1-yl) butyl]phosphonate

The title substance was prepared from diethyl [3-(3-methylxanthin-1-yl)pentyl]phosphonate (0.008 mol, Example 43) and methoxyethyl chloride analogously to Example 30.

Yield: 3.1 g (90% of theory), melting point: 110° C., $C_{15}H_{25}N_4O_6P$ (MW=430.4), $^1$H-NMR (CDCl$_3$) δ=1.30 (t, 6H); 1.33 (t, 3H); 1.60–1.78 (m, 6H); 3.32 (s, 3H); 3.69 (t, 2H); 3.93–4.21 (m, 8H); 4.45 (t, 2H); 7.61 (s, 1H) ppm

EXAMPLE 46

Diethyl [3-(7-cyclopropylmethyl-3-methylxanthin-1-yl)propyl]phosphonate

The title substance was prepared from 0.015 mol of diethyl [3-(3-methyl-xanthin-1-yl)propyl]phosphonate (Example 42), and 0.017 mol of chloromethylcyclopropane analogously to Example 30 and chromatographed on silica gel (eluent: dichloromethane/methanol 20:1).

Yield: 3.5 g (59% of theory), melting point: 86°–87° C., $C_{17}H_{27}N_4O_5P$ (MW=398.4), $^1$H-NMR (CDCl$_3$) δ=0.38–0.45 (m, 2H); 0.60–0.71 (m, 2H); 1.30 (t, 6H); 1.25–1.40 (m, 1H); 1.70–2.05 (m, 4H); 3.57 (s, 3H); 4.00–4.19 (m, 8H); 7.64 (s, 1H) ppm

EXAMPLE 47

Diethyl [3-(7-methylethylxanthin-1-yl)propyl] phosphonate

The title substance was prepared from 0.02 mol of 7-isopropyl-3-methyl-xanthine and 0.022 mol of diethyl 3-bromopropanephosphonate analogously to Example 46.

Yield: 5.4 g (70% of theory), melting point: 134° C., $C_{16}H_{27}N_4O_5P$ (MG=386.4), $^1$H-NMR (CDCl$_3$) δ=1.31 (t, 6H); 1.57 (d, 6H); 1.65–2.05 (m, 4H); 3.57 (s, 3H); 4.02–4.18 (m, 6H); 5.02 (s, 1H); 7.65 (s, 1H) ppm

EXAMPLE 48

Diethyl [5-(7-butyl-3-methylxanthin-1-yl)pentyl] phosphonate

The title substance was prepared from 0.008 mol of diethyl [5-(3-methyl-xanthin-1-yl)pentyl]phosphonate and 0.01 mol of 1-bromobutane analogously to Example 46.

Yield: 2.9 g (85% of theory), oil, $C_{19}H_{33}N_4O_5P$ (MW= 428.5), $^1$H-NMR (CDCl$_3$) δ=0.94 (t, 3H); 1.29 (t, 6H); 1.29–1.95 (m, 12H); 3.55 (s, 3H); 3.93–4.14 (m, 6H); 4.26 (t, 2H); 7.51 (s, 1H) ppm

EXAMPLE 49

Diethyl [5-(7-cyclopropylmethyl-3-methylxanthin-1-yl)pentyl]phosphonate

The title substance was prepared from 0.011 mol of diethyl [5-(3-methyl-xanthin-1-yl)pentyl]phosphonate and 0.013 mol of chloromethylcyclo-propane analogously to Example 46.

Yield: 2.7 g (58% of theory), oil, $C_{19}H_{31}N_4O_5P$ (MW= 426.5), $^1$H-NMR (CDCl$_3$) δ=0.35–0.45 (m, 2H); 0.60–0.70 (m, 2H); 1.28 (t, 6H); 1.31–1.78 (m, 9H); 3.55 (s, 3H); 3.92–4.18 (m, 8H); 7.62 (s, 1H) ppm

EXAMPLE 50

Diethyl [4-(7-cyclopropylmethyl-3-methylxanthin-1-yl)butyl]phosphonate

The title substance was prepared from 0.016 mol of diethyl [5-(3-methyl-xanthin-1-yl)butyl]phosphonate and 0.02 mol of chloromethylcyclopropane analogously to Example 46.

Yield: 4.8 g (73% of theory), melting point: 104° C., $C_{18}H_{29}N_4O_5P$ (MW=412.4), $^1$H-NMR (CDCl$_3$) δ=0.38–0.48 (m, 2H); 0.62–0.72 (m, 2H); 1.30 (t, 6H); 1.30–1.42 (m, 1H); 1.60–1.88 (m, 6H); 3.57 (s, 3H); 3.98–4.20 (m, 8H); 7.63 (s, 1H) ppm

EXAMPLE 51

Diethyl {4-[7-(2-methylpropyl)-3-methylxanthin-1-yl]butyl}phosphonate

The title substance was prepared from 0.016 mol of diethyl [5-(3-methyl-xanthin-1-yl)butyl]phosphonate and 0.02 mol of 1-bromo-2-methylpropane analogously to Example 46 and crystallized from ethyl acetate/diisopropyl ether.

Yield: 3.5 g (53% of theory), melting point: 80° C., $C_{18}H_{31}N_4O_5P$ (MW=414.45), $^1$H-NMR (CDCl$_3$) δ=0.93 (d, 6H); 1.30 (t, 6H); 1.60–1.88 (m, 6H); 2.21 (s, 1H); 3.56 (s, 3H); 3.95–4.18 (m, 8H); 7.49 (s, 1H) ppm

EXAMPLE 52

Diethyl [4-(7-methylethylxanthin-1-yl)butyl] phosphonate

The title substance was prepared from diethyl 5-(3-methyl-xanthin-1-yl)-butyl]phosphonate and 0.02 mol of 2-bromopropane analogously to Example 46.

Yield: 4.7 g (73% of theory), melting point: 78°–80° C., $C_{17}H_{29}N_4O_5P$ (MW=400.4), $^1$H-NMR (CDCl$_3$) δ=1.29 (t, 6H); 1.56 (d, 6H); 1.65–2.05 (m, 6H); 3.56 (s, 3H); 4.00–4.18 (m, 6H); 5.02 (se, 1H); 7.63 (s, 1H) ppm

EXAMPLE 53

Diethyl [4-(3-benzyl-7-ethoxymethylxanthin-1-yl) butyl]phosphonate a) 3-Benzyl-7-ethoxymethylxanthine The title substance was prepared analogously to 7-ethoxymethyl-3-methylxanthine (Example 3).

Yield: 12.3 g (82% of theory), $C_9H_{16}N_4O_3$ (MW=300.3)

b) Diethyl [4-(3-benzyl-7-ethoxymethylxanthin-1-yl) butyl]phosphonate

The title substance was prepared from 0.037 mol of 3-benzyl-7-ethoxy-methylxanthine und 0.045 mol of diethyl 4-chlorobutanephosphonate analogously to Example 23 and chromatographed on silica gel. (Eluent: dichloromethane/methanol 20:1).

Yield: 8.8 g (48% of theory), oil, $C_{23}H_{33}N_4O_6P$ (MW= 492.5), $^1$H-NMR (CDCl$_3$) δ=1.10–1.35 (m, 9H); 1.55–1.94 (m, 6H); 3.61 (q, 2H); 3.93–4.18 (m, 6H); 5.26 (s, 2H); 5.67 (s, 2H); 7.22–7.38 (m, 3H); 7.43–7.53 (m, 2H); 7.74 (s, 1H) ppm

EXAMPLE 54

Diethyl [4-(7-ethoxymethyl-3-ethylxanthin-1-yl) butyl]phosphonate a) 7-Ethoxymethyl-3-ethylxanthine The title substance was prepared analogously to Example 53a).

Yield: 4.5 g (70% of theory), $C_{10}H_{14}N_4O_3$ (MW=236.2)

b) Diethyl [4-(7-ethoxymethyl-3-ethylxanthin-1-yl)butyl] phosphonate

The title substance was prepared from 0.01 5 mol of 7-ethoxymethyl-3-ethylxanthine and 0.017 mol of diethyl 4-chlorobutanephosphonate analogously to 53.

Yield: 5.03 g (78% of theory), melting point: 80° C., $C_{18}H_{31}N_4O_6P$ (MW=430.4), $^1$H-NMR (CDCl$_3$) δ=1.20 (t, 3H); 1.30 (t, 6H); 1.33 (t, 3H); 1.58–1.90 (m, 6H); 3.62 (q, 2H); 3.95–4.22 (m, 8H); 5.68 (s, 2H); 7.73 (s, 1H) ppm

EXAMPLE 55

Diethyl [3-(3-methyl-7-propylxanthin-1-yl)propyl] phosphonate

The title substance was prepared from 0.048 mol of 3-methyl-7-propyl-xanthine and 0.058 mol of diethyl 3-bromopropanephosphonate analogously to Example 23.

Yield: 14.7 g (79% of theory), melting point: 77°–79° C., $C_{16}H_{27}N_4O_5P$ (MW=386.4), $^1$H-NMR (CDCl$_3$) δ=0.93 (t, 3H); 1.29 (t, 6H); 1.70–2.05 (m, 6H); 3.56 (s, 3H); 4.00–4.18 (m, 6H); 4.23 (t, 2H); 7.52 (s, 1H) ppm

EXAMPLE 56

Diethyl 5-[7-(3-methylbutyl)-3-methylxanthin-1-yl) propyl]phosphonate

The title substance was prepared from 0.025 mol of 7-(3-methylbutyl)-3-methylxanthine (see Example 41) and 0.028 mol of diethyl 5-bromo-pentanephosphonate analogously to Example 46.

Yield: 4.8 g (43% of theory), oil, $C_{20}H_{35}N_4O_5P$ (MW= 442.5), $^1$H-NMR (CDCl$_3$) δ=0.96 (d, 6H); 1.30 (t, 6H);

1.36–1.84 (m, 11H); 3.56 (s, 3H); 3.93–4.12 (m, 6H); 4.30 (t, 2H); 7.52 (s, 1H) ppm

EXAMPLE 57

Diethyl [5-(3-ethyl-7-propylxanthin-1-yl)pentyl] phosphonate

The title substance was prepared from 0.0225 mol of 3-ethyl-7-propyl-xanthine and 0.027 mol of diethyl 5-bromopentanephosphonate analogously to Example 46.

Yield: 3 g (31% of theory), oil, $C_{19}H_{33}N_4O_5P$ (MW=428.5), $^1$H-NMR (CDCl$_3$) δ=0.93 (t, 3H); 1.28 (t, 6H); 1.32 (t, 3H); 1.40–1.93 (m, 10H); 3.90–4.23 (m, 1 OH); 7.50 (s, 1H) ppm

EXAMPLE 58

Diethyl [4-(8-bromo-3-methylxanthin-1-yl)-propyl] phosphonate 12.15 g (0.076 mol) of bromine were added dropwise at 20° C. to a solution of 20 g (0.058 mol) of diethyl [3-(3-methylxanthin-1-yl)propyl]phosphonate (Example 42) and 6.24 g (0.076 mol) of sodium acetate in 150 ml of acetic acid. The acetic acid was evaporated, the residue was taken up in dichloromethane, and the solution was washed with sodium thiosulfate solution and water, and dried over sodium sulfate. It was evaporated under reduced pressure, and the residue was dried and crystallized from water.

Yield: 19.3 g (79% of theory), melting point: 190°–192° C., $C_{13}H_{20}BrN_4O_5P$ (MW=423.2), $^1$H-NMR (CDCl$_3$) δ=1.31 (t, 6H); 1.78–2.13 (m, 4H); 3.58 (s, 3H); 4.02–4.18 (m, 6H); 13.60 (s, 1H, NH) ppm

EXAMPLE 59

[1-(3,7-Dimethylxanthin-1-yl)methyl] dimethylphosphine Oxide

A solution of 20.2 g (0.1 mol) of theophylline sodium salt in 400 ml of DMF was heated at 130° C. for 3 hours with 12.7 g of chloromethyldimethyl-phosphine oxide. The solution was filtered, the solvent was evaporated and the residue was taken up in methanol. The precipitate was filtered off and dried to constant weight under reduced pressure.

Yield: 17.2 g (64% of theory), melting point: 250°–252° C., $C_{10}H_{15}N_4O_3P$ (MW=270.2)

EXAMPLE 60

[1-(1,3-Dimethylxanthin-7-yl)methyl] dimethylphosphine Oxide

The title substance was prepared from 20.2 g (0.1 mol) of theobromine sodium salt and chloromethyldimethylphosphine oxide analogously to Example 59 and crystallized from ethyl acetate.

Yield: 23 g (87% of theory), melting point: 206°–210° C., $C_{10}H_{15}N_4O_3P$ (MW=270.2)

EXAMPLE 61

[1-(7-Dimethylphosphinyl-3-methylxanthin-1-yl) methyl]dimethylphosphine Oxide

The title substance was prepared from 22 g (0.1 mol) of 3-methylxanthine disodium salt and chloromethyldimethylphosphine oxide analogously to Example 59 and crystallized from methanol.

Yield: 30 g (86% of theory), melting point: 250°–254° C., $C_{12}H_{20}N_4O_4P$ (MW=346.3)

EXAMPLE 62

[1-(1-Hexyl-3-methylxanthin-7-yl)methyl] dimethylphosphine Oxide

The title substance was prepared from 26 g (0.1 mol) of 1-hexyl-3-methylxanthine sodium salt and chloromethyldimethylphosphine oxide analogously to Example 59 and crystallized from hexane.

Yield: 19 g (56% of theory), melting point: 132°–135° C., $C_{15}H_{25}N_4O_3P$ (MW=340.4)

EXAMPLE 63

[1-(8-Bromo-3,7-dimethylxanthin-1-yl)methyl] dimethylphosphine Oxide

The title substance was prepared from 28 g (0.1 mol) of 8-bromo-3,7-dimethylxanthine sodium salt and chloromethyldimethylphosphine oxide analogously to Example 59 and chromatographed on silica gel.

Yield: 9.6 g (34% of theory), melting point: 268°–272° C., $C_{10}H_{14}BrN_4O_3P$ (MW=349.1)

EXAMPLE 64

[4-(1,3-Dimethylxanthin-7-yl)butyl] dimethylphosphine Oxide

The title substance was prepared from 10.1 g (0.05 mol) of 1,3-dimethyl-xanthine sodium salt and 4-chlorobutyldimethylphosphine oxide analogously to Example 63.

Yield: 5.5 g (35% of theory), melting point: 195°–203° C., $C_{13}H_{21}N_4O_3P$ (MW=312.31)

EXAMPLE 65

[1-(3,7-Dimethylxanthin-1-yl)methyl] dimethylphosphine Oxide

The title substance was prepared from 10.1 g (0.05 mol) of 3,7-dimethylxanthine sodium salt and 4-chlorobutyldimethylphosphine oxide analogously to Example 63.

Yield: 2.5 g (16% of theory), melting point: 148°–150° C., $C_{13}H_{21}N_4O_3P$ (MW=312.3)

EXAMPLE 66

[3-(3,7-Dimethylxanthin-1-yl)propyl] dimethylphosphine Oxide

The title substance was prepared from 10.1 g (0.05 mol) of 3,7-di-methylxanthine sodium salt and 3-chloropropyldimethylphosphine oxide analogously to Example 59 and crystallized from ethyl acetate.

Yield: 4 g (27% of theory), melting point: 167°–168° C., $C_{12}H_{19}N_4O_3P$ (MW=298.3)

EXAMPLE 67

[1-(1,3-Dibutylxanthin-7-yl)methyl] dimethylphosphine Oxide 5 g (0.01 9 mol) of 1,3-dibutylxanthine were stirred at 80° C. for 6 hours with 2.88 g (0.0228 mol) of chloromethyldimethylphosphine oxide and 3.2 g (0.0228 mol) of potassium carbonate in 80 ml of DMF. The solution was cooled to room temperature and filtered, and the filtrate was concentrated under reduced pressure. The residue which remained was crystallized in petroleum ether/ethyl acetate.

Yield: 4 g (59% of theory), melting point: 148° C., $C_{16}H_{27}N_4O_3P$ (MW=354.4), $^1$H-NMR (CDCl$_3$) δ=0.95 (t, 3H); 0.97 (t, 3H); 1.30–1.73 (m, 14H); 4.00 (t, 2H); 4.12 (t, 2H); 4.82 (d, 2H); 7.85 (s, 1H) ppm

EXAMPLE 68

[1-(1,3-Dipropylxanthin-7-yl)methyl] dimethylphosphine Oxide

The title substance was prepared from 5 g (0.0186 mol) of 1,3-dipropyl-xanthine and 2.8 g (0.0224 mol) of chloromethyldimethylphosphine oxide analogously to Example 67.

Yield: 4.9 g (82% of theory), melting point: 172° C., $C_{14}H_{23}N_4O_3P$ (MW=326.3), $^1$H-NMR (CDCl$_3$) δ=0.94 (t, 3H); 0.97 (t, 3H); 1.57 (d, 6H); 1.57–1.88 (m, 4H); 3.91–4.12 (m, 4H); 4.81 (d, 2H); 7.84 (d, 1H) ppm

EXAMPLE 69

[1-(7-Benzyl-3-phenylxanthin-1-yl)methyl] dimethylphosphine Oxide a) 7-Benzyl-3-phenylxanthine 3.2 g (0.1315 mol) of sodium hydride were added in portions to a suspension of 30 g (0.1315 mol) of 3-phenylxanthine in 600 ml of DMF, the mixture was stirred at 25° C. for 30 minutes and then heated to 80° C. 27 g (0.1578 mol) of benzyl bromide were then added and the solution was left at 80° C. for 6 hours. After cooling to 50° C., the reaction mixture was poured into 2000 ml of ice-water, and the precipitate obtained was filtered off with suction, washed well with water and dried under reduced pressure. The dry residue was crystallized from dioxane/methanol.

Yield: 27 g (63% of theory), melting point: 246° C., $C_{18}H_{14}N_4O_2$ (MW=318.3)

b) [1-(7-Benzyl-3-phenylxanthin-1-yl)methyl] dimethylphosphine oxide

The title substance was prepared from 6.5 g (0.02 mol) of 7-benzyl-3-phenylxanthine and 3.1 g (0.0245 mol) of chloromethyldimethylphosphine oxide analogously to Example 67.

Yield: 6.5 g (78% of theory), melting point: 232°–234° C., $C_{21}H_{21}N_4O_3P$ (MW=408.4). $^1$H-NMR (CDCl$_3$) δ=1.62 (d, 6H); 4.53 (d, 2H); 5.51 (s, 2H); 7.37–7.58 (m, 11H) ppm

EXAMPLE 70

[1-(3-Phenylxanthin-1-yl)methyl]dimethylphosphine Oxide 6.4 g (0.0157 mol) of 1-(7-benzyl-3-phenylxanthin-1-yl) methyl]-dimethylphosphine oxide were hydrogenated analogously to Example 24.

Yield: 3.9 g (61% of theory), melting point: 312°–314° C., $C_{14}H_{15}N_4O_3P$ (MW=318.3), $^1$H-NMR (CDCl$_3$) δ=1.49 (d, 6H); 4.32 (d, 2H); 7.40–7.59 (m, 5H); 8.00 (s, 1H); 13.75 (s, 1H, NH) ppm

EXAMPLE 71

[1-(7-Cyclopropylmethyl-3-phenylxanthin-1-yl) methyl]dimethylphosphine Oxide 3.9 g (0.0123 mol) of [1-(3-phenylxanthin-1-yl)methyl] dimethylphosphine oxide (Example 70) were stirred at 70° C. for 6 hours with 1.33 g (0.0147 mol) of chloromethylcyclopropane and 2 g of potassium carbonate. The solution was filtered and concentrated, and the residue which remained was chromatographed on silica gel (eluent: ethyl acetate/methanol 10:1).

Yield: 2.5 g (55% of theory), melting point: 226° C., $C_{18}H_{21}N_4O_3P$ (MW=372.4), $^1$H-NMR (CDCl$_3$) δ=0.40–0.49 (m, 2H); 0.63–0.72 (m, 2H); 1.27–1.45 (m, 1H); 1.63 (d, 6H); 4.19 (d, 2H); 4.53 (d, 2H); 7.40–7.60 (m, 5H); 7.61 (s, 1H) ppm

EXAMPLE 72

[1-(3,7-Dibutylxanthin-1-yl)methyl] dimethylphosphine Oxide

The title substance was prepared from 5 g (0.0189 mol) of 3,7-dibutyl-xanthine and 2.9 g (0.0227 mol) of chloromethyldimethylphosphine oxide analogously to Example 67.

Yield: 4.3 g (64% of theory), melting point: 124° C., $C_{16}H_{27}N_4O_3P$ (MW=354.4), $^1$H-NMR (CDCl$_3$) δ=0.95 (t, 6H); 1.22–1.48 (m, 4H); 1.60 (d, 6H); 1.63–1.92 (m, 4H); 4.10 (t, 2H); 4.28 (t, 2H); 4.49 (d, 2H); 7.54 (s, 1H) ppm

EXAMPLE 73

[1-(3-Cyclopropyl-7-propylxanthin-1-yl)methyl] dimethylphosphine Oxide

The title substance was prepared from 3.2 g (0.0137 mol) of 3-cyclopropyl-7-propylxanthine (see Example 39) and 2.07 g (0.0164 mol) of chloro-methyldimethylphosphine oxide analogously to Example 67.

Yield: 3.6 g (81% of theory), melting point: 177°–179° C., $C_{14}H_{21}N_4O_3P$ (MW=324.3), $^1$H-NMR (CDCl$_3$) δ=0.93 (t, 3H); 0.95–1.25 (m, 4H); 1.60 (d, 6H); 1.82–1.95 (m, 2H); 2.95–3.06 (m, 1H); 4.23 (t, 2H); 4.46 (d, 2H); 7.56 (s, 1H) ppm

EXAMPLE 74

[1-(7-Ethyl-3-methylxanthin-1-yl)methyl] dimethylphosphine Oxide

The title substance was prepared from 5 g (0.0258 mol) of 7-ethyl-3-methylxanthine and 3.91 g (0.031 mol) of chloromethyl-dimethylphosphine oxide analogously to Example 67.

Yield: 6 g (82% of theory), melting point: 164° C., $C_{11}H_{17}N_4O_3P$ (MW=284.3), $^1$H-NMR (CDCl$_3$) δ=1.50 (t, 3H); 1.61 (d, 6H); 3.58 (s, 3H); 4.33 (q, 2H); 4.80 (d, 2H); 7.58 (s, 1H) ppm

Pharmacological Tests

1. Activity in the rat muscle function test

Male Wistar rats (body weight about 300 g) were kept under standard conditions with feed and water ad libitum. The right rear extremity was immobilized by fitting a kind of "shoe" to the animals under short-term anaesthesia. Two ergonomically fitted halves of the "shoe" were cast from a liquid plastic material which is also used for the production of dental prostheses, these were put onto the animal under brief anaesthesia and joined with the aid of a wire. The material is light but hard, so that the animals cannot gnaw the material, and the "shoe" can be opened at any time to examine the condition of the immobilized extremity. The two halves were moreover padded out with chamois leather in order to avoid compressions and possible injuries due to rubbing. The system also has the advantage that the angle of immobilization is standardized in all animals; this would not be possible with a plaster cast. The chosen angle allows the animals to take up a normal sitting position despite the "shoe" and also to carry the body weight using this extremity. Only complete stretching or bending of the leg is impossible.

During the 3 weeks' immobilization, the animals showed normal behavior, normal body weight development and ambulation in the cage. In spite of this, a significant decrease in the skeletal muscle mass (atrophy) of the immobilized extremity occurred, to be precise up to −35% in comparison with the contralateral nonimmobilized rear extremity. As the soleus muscle was the most severely affected, the changes in muscle weight after administration of preparation shown in Table 1 relate to this muscle. A difference of ≦25% between the right immobilized and left non-immobilized rear extremity was classified as an effect.

After 3 weeks' immobilization of the right rear extremity and simultaneous oral administration of test preparations (1× per day using a stomach tube; as a rule 25 mg/kg of body weight, in carboxymethylcellulose, the animals were weighed and anaesthetized with pentobarbital (35 mg/kg i.p.). Functional parameters were measured during direct electrical stimulation of a muscle group (gastrocnemius, plantaris and soleus). This muscle group, merely called "muscle" in the following, was exposed at the ankle tendon and tied to a force transducer via the tendon.

To determine the contractile force, the muscles were stimulated isometrically, i.e. a preload of 0.5N was applied and the muscle was stimulated by means of a series of electrical pulses, which led to a maximum contraction, every 0.7 sec for 80 msec for a period of 15 min. Over time, the contraction curve decreases on account of the tiredness of the muscle, the decrease for the atrophic muscle being significantly greater than the decrease for the contralateral normal muscle. The area under this contraction curve was evaluated and the difference in percent between the right atrophic and left normal muscle compared (force under the contraction curve as difference in percent (Δ%)). The difference in the control group is approximately 25%.

An isotonic muscle stimulation was used to determine the performed work of the muscle over time. In this type of measurement, the shortening of the muscle during contraction is used as a basis. To this end, a preload which corresponds to the body weight was applied to the muscles. A series of stimulation pulses (80 msec) were triggered every 3 sec and the muscle was stimulated for 15 min. The data (contraction force and distance travelled) were converted to the work performed in the unit J using an automated system. The difference in the work performed between the immobilized atrophic and the normal muscle in the control animals was approximately −25%.

A preparation which showed a right/left difference of ≦−12% (Δ%) in isotonic and/or isometric function measurement was classified as active. Values which are positive indicate that the functional parameters of the immobilized muscle were better than those of the contralateral normal muscle.

The results are shown in Table I.

TABLE I

| Example | Structure | Force (Δ %) | Work (Δ %) | Muscle weight (Δ %) |
| --- | --- | --- | --- | --- |
| 1 | 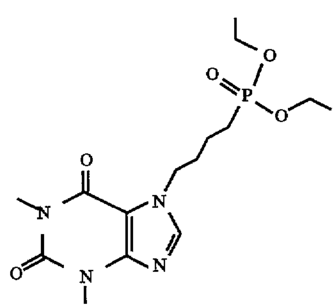 | ±0 | −8 | n.d. |
| 2 | 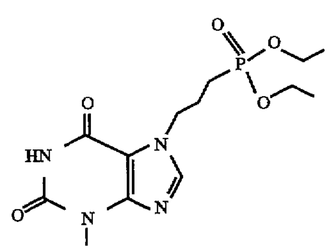 | ±0 | +5 | −22 |

TABLE I-continued

| Example | Structure | Force (Δ %) | Work (Δ %) | Muscle weight (Δ %) |
|---|---|---|---|---|
| 3 | 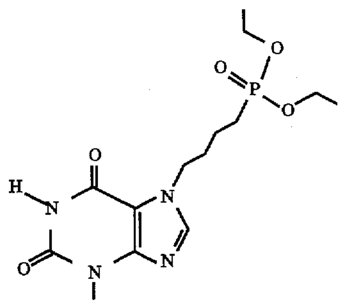 | 0 | 0 | 0 |
| 4 | 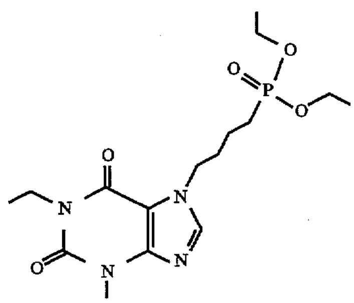 | n.d. | n.d. | n.d. |
| 5 | 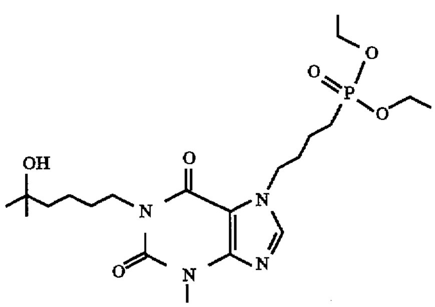 | +10 | +10 | 0 |
| 6 | 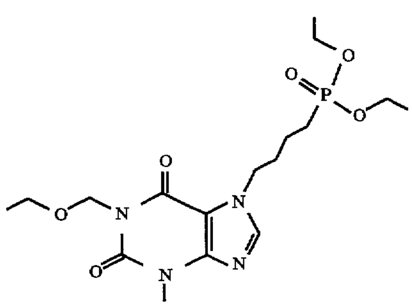 | −4 | −4 | 0 |

TABLE I-continued

| Example | Structure | Force (Δ %) | Work (Δ %) | Muscle weight (Δ %) |
|---|---|---|---|---|
| 7 | 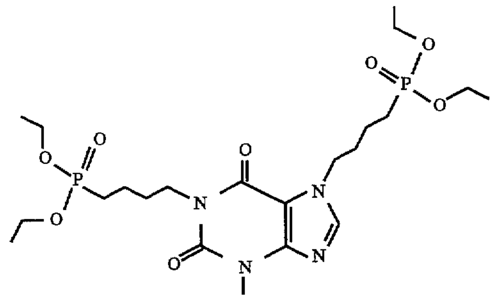 | n.d. | n.d. | n.d. |
| 8 | 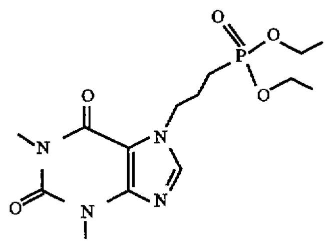 | −11 | −7 | n.d. |
| 9 | 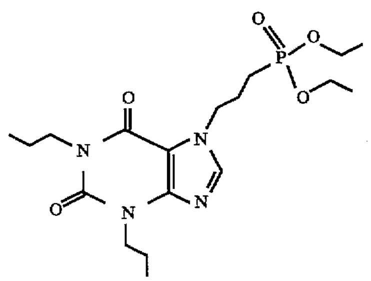 | n.d. | n.d. | n.d. |
| 10 | 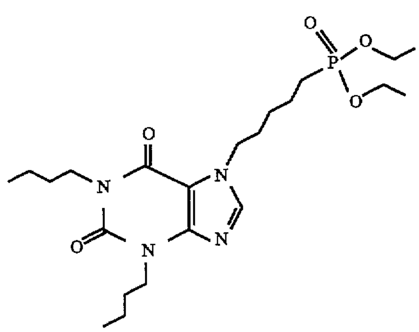 | +1 | −9 | −13 |
| 11 | 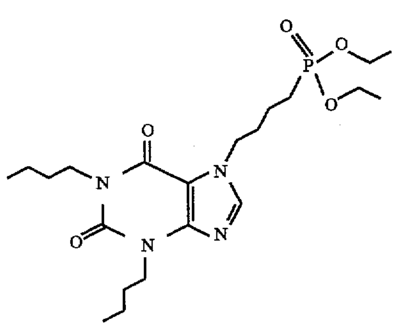 | n.d. | n.d. | n.d. |

TABLE I-continued

| Example | Structure | Force (Δ %) | Work (Δ %) | Muscle weight (Δ %) |
|---|---|---|---|---|
| 12 | (structure) | n.d. | n.d. | n.d. |
| 13 | (structure) | +5 | −3 | −24 |
| 14 | (structure) | n.d. | n.d. | n.d. |
| 15 | (structure) | +5 | +2 | 0 |
| 16 | (structure) | n.d. | n.d. | n.d. |

TABLE I-continued
| Example | Structure | Force (Δ %) | Work (Δ %) | Muscle weight (Δ %) |
|---|---|---|---|---|
| 17 | 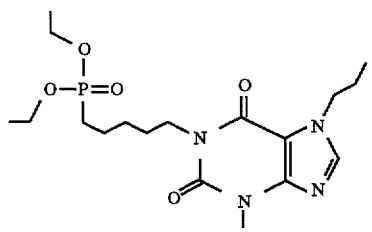 | +2 | −10 | 0 |
| 18 | 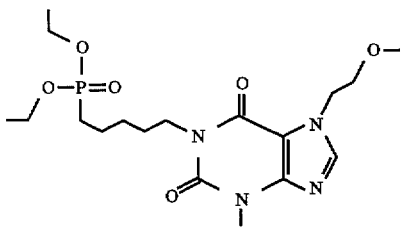 | n.d. | n.d. | n.d. |
| 19 | 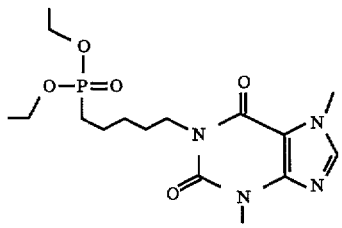 | n.d. | n.d. | n.d. |
| 20 | 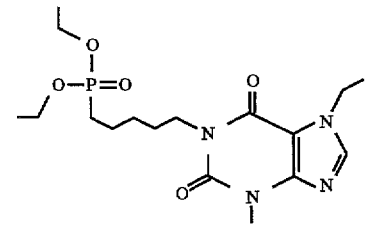 | n.d. | n.d. | n.d. |
| 21 | 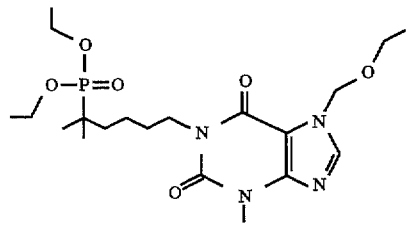 | n.d. | n.d. | n.d. |
| 22 | 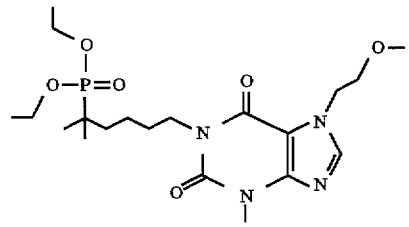 | −3 | −13 | 0 |

TABLE I-continued
| Example | Structure | Force (Δ %) | Work (Δ %) | Muscle weight (Δ %) |
|---|---|---|---|---|
| 23 | 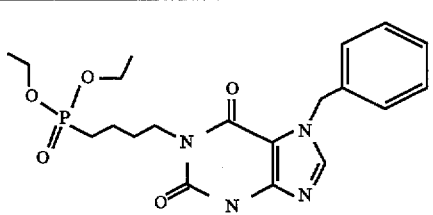 | n.d. | n.d. | n.d. |
| 24 | 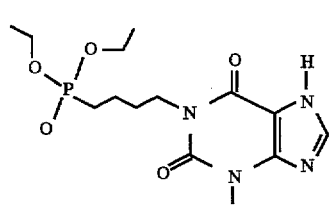 | +6 | −5 | −20 |
| 25 | 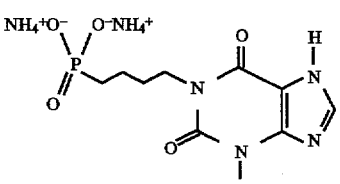 | +7 | −12 | n.d. |
| 26 | 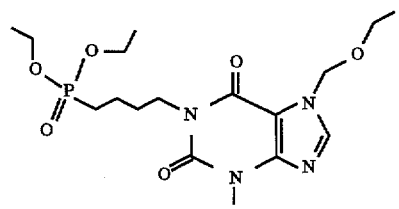 | −3 | −17 | −22 |
| 27 | 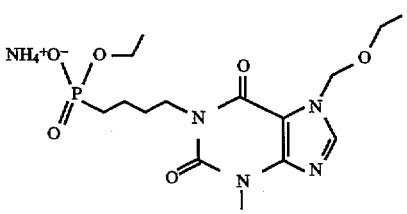 | n.d. | n.d. | n.d. |
| 28 | 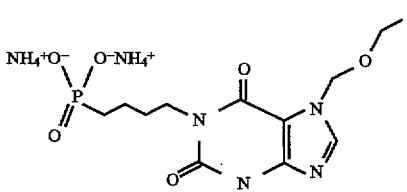 | n.d. | n.d. | n.d. |

TABLE I-continued

| Example | Structure | Force (Δ %) | Work (Δ %) | Muscle weight (Δ %) |
|---|---|---|---|---|
| 29 | 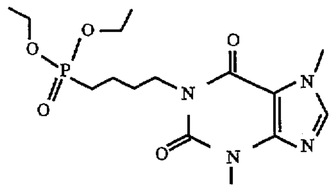 | n.d. | n.d. | n.d. |
| 30 | 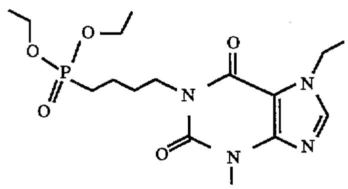 | +2 | +5 | 0 |
| 31 | 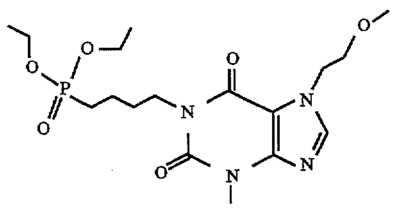 | n.d. | n.d. | n.d. |
| 32 | 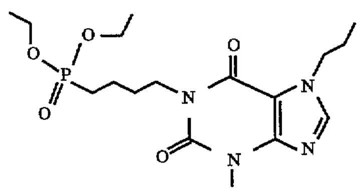 | −9 | −1 | 0 |
| 33 | 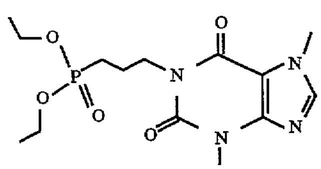 | −7 | −10 | −16 |
| 34 | 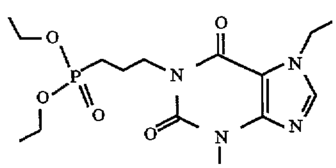 | −5 | −11 | n.d. |
| 35 | 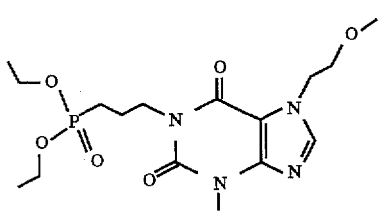 | n.d. | n.d. | n.d. |

TABLE I-continued
| Example | Structure | Force (Δ %) | Work (Δ %) | Muscle weight (Δ %) |
|---|---|---|---|---|
| 36 | 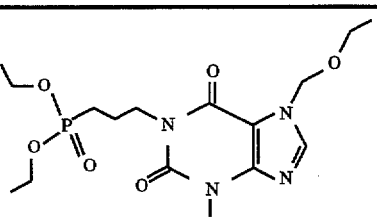 | n.d. | n.d. | n.d. |
| 37 | 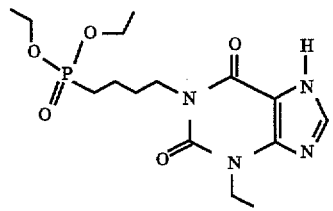 | n.d. | n.d. | n.d. |
| 38 | 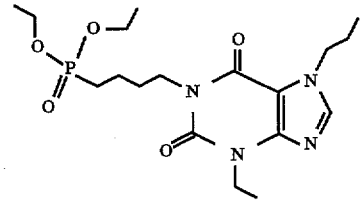 | −10 | −3 | n.d. |
| 39 | 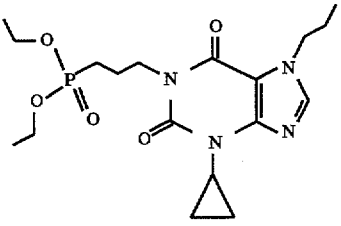 | n.d. | n.d. | n.d. |
| 40 | 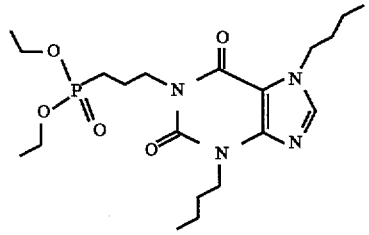 | n.d. | n.d. | n.d. |
| 41 | 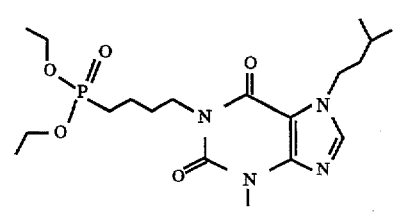 | n.d. | n.d. | n.d. |
| 42 | 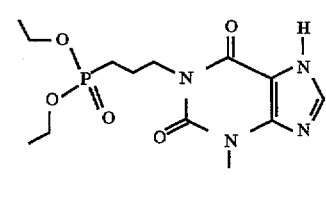 | n.d. | n.d. | n.d. |

TABLE I-continued

| Example | Structure | Force (Δ %) | Work (Δ %) | Muscle weight (Δ %) |
|---------|-----------|-------------|------------|---------------------|
| 43 | 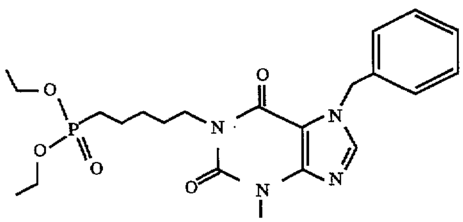 | n.d. | n.d. | n.d. |
| 44 | 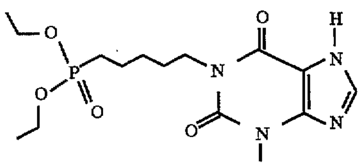 | n.d. | n.d. | n.d. |
| 45 | 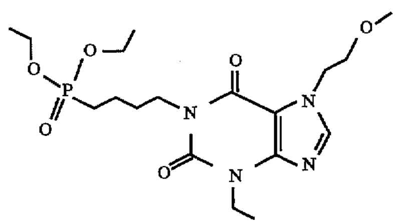 | n.d. | n.d. | n.d. |
| 46 | 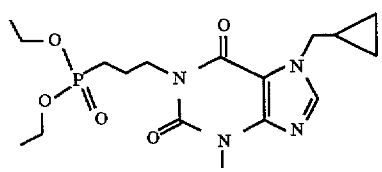 | +1 | +9 | −17 |
| 47 | 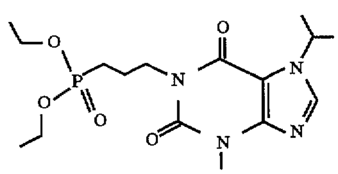 | ±0 | −6 | 0 |
| 48 | 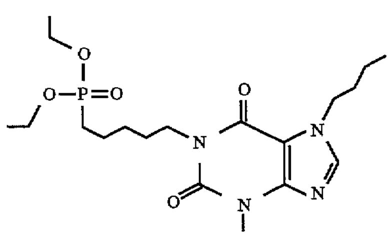 | −3 | −7 | 0 |

TABLE I-continued

| Example | Structure | Force (Δ %) | Work (Δ %) | Muscle weight (Δ %) |
|---|---|---|---|---|
| 49 | 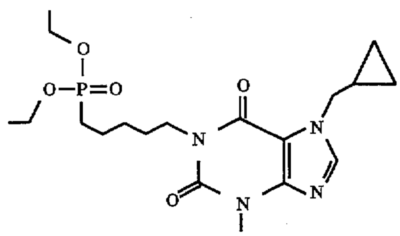 | −5 | −5 | −25 |
| 50 | 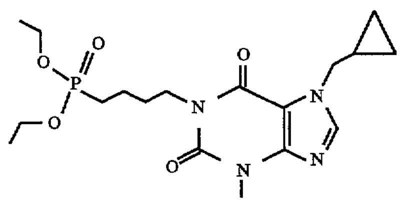 | n.d. | n.d. | n.d. |
| 51 | 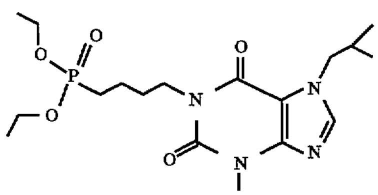 | n.d. | n.d. | n.d. |
| 52 | 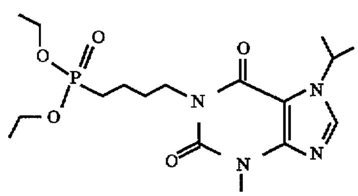 | n.d. | n.d. | n.d. |
| 53 | 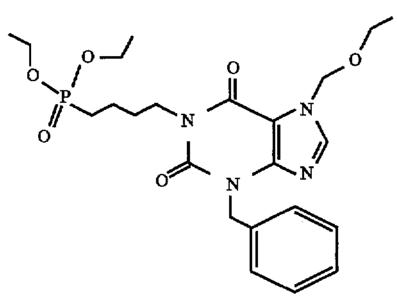 | −3 | +10 | 0 |
| 54 | 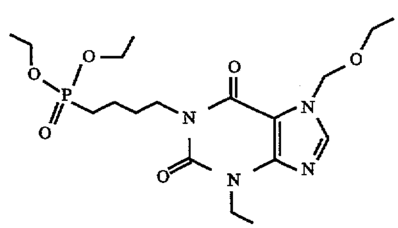 | n.d. | n.d. | n.d. |

TABLE I-continued

| Example | Structure | Force (Δ %) | Work (Δ %) | Muscle weight (Δ %) |
|---------|-----------|-------------|------------|---------------------|
| 55 | 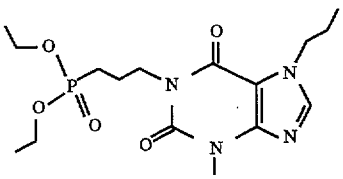 | n.d. | n.d. | n.d. |
| 56 | 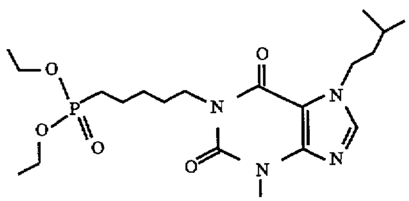 | 0 | 0 | n.d. |
| 57 | 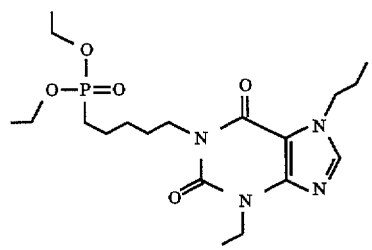 | −5 | −8 | −17 |
| 58 | 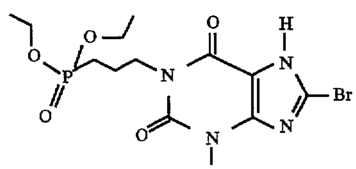 | n.d. | n.d. | n.d. |
| 59 | 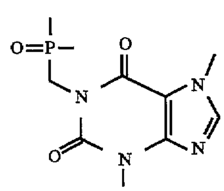 | n.d. | n.d. | n.d. |
| 60 | 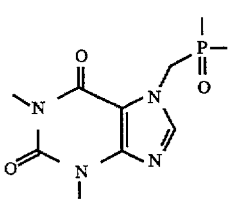 | n.d. | n.d. | n.d. |
| 61 | 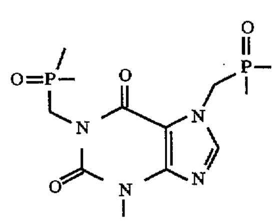 | n.d. | n.d. | n.d. |

TABLE I-continued

| Example | Structure | Force (Δ %) | Work (Δ %) | Muscle weight (Δ %) |
|---|---|---|---|---|
| 62 | 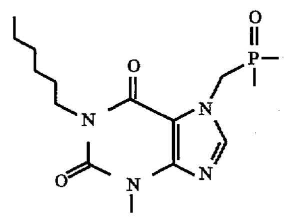 | n.d. | n.d. | n.d. |
| 63 | 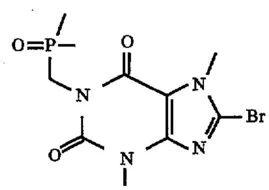 | n.d. | n.d. | n.d. |
| 64 | 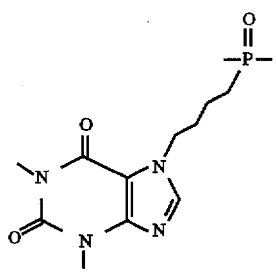 | n.d. | n.d. | n.d. |
| 65 | 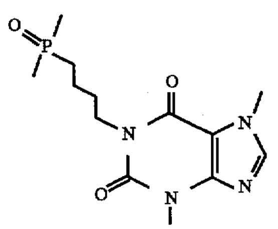 | n.d. | n.d. | n.d. |
| 66 | 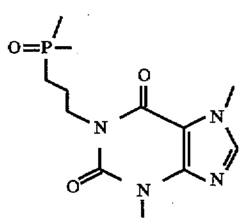 | n.d. | n.d. | n.d. |
| 67 | 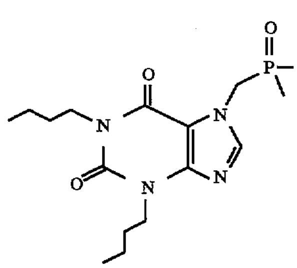 | −9 | −10 | n.d. |

TABLE I-continued

| Example | Structure | Force (Δ %) | Work (Δ %) | Muscle weight (Δ %) |
|---------|-----------|-------------|------------|---------------------|
| 68 | 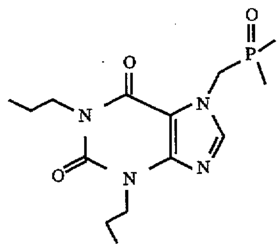 | n.d. | n.d. | n.d. |
| 69 | 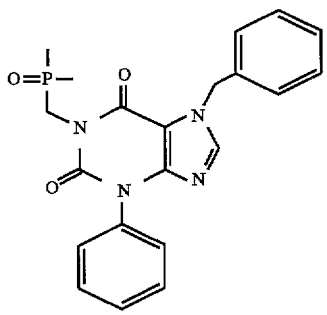 | n.d. | n.d. | n.d. |
| 70 | 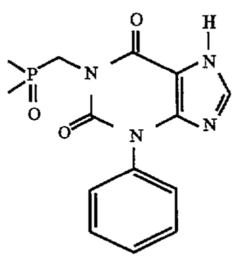 | n.d. | n.d. | n.d. |
| 71 | 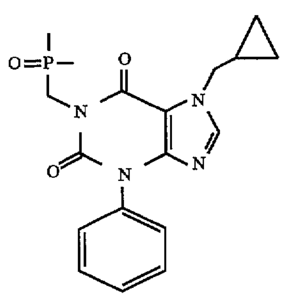 | +4 | +5 | 0 |
| 72 | 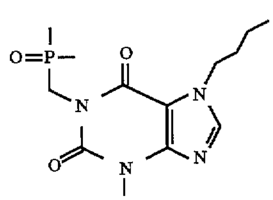 | −2 | +4 | −18 |

TABLE I-continued

| Example | Structure | Force (Δ %) | Work (Δ %) | Muscle weight (Δ %) |
|---|---|---|---|---|
| 73 | 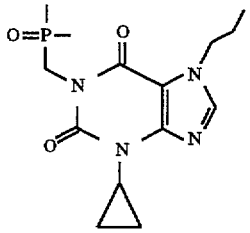 | n.d. | n.d. | n.d. |
| 74 | 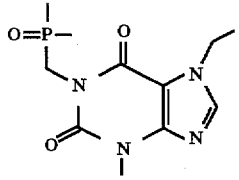 | n.d. | n.d. | n.d. |

2. Test for effect on endotoxin fatality

Individual injections of lipopolysaccharide (LPS), from gram-negative bacteria, lead via a series of various symptoms to septic shock, which usually turns out to be fatal. Endotoxin (LPS) from Salmonella abortus equi in a dose of 60 mg/kg i.p. leads to shock and to death with at most 72 h p.a. (the dose of 60 mg/kg corresponds to approximately 1.20 mg of LPS/animal).

The experimental animals used are female NMRI mice from the Hoechst AG/Hattersheim animal breeding unit having a body weight of 22 to 24 g.

The test substances administered intraperitoneally (i.p.) in an administration volume of 10 ml/kg at the same time as the LPS. The number of surviving animals after 72 hours' LPS administration is indicated in comparison to a placebo control. The number of tested animals per group is 5; dose 25 mg/kg. The results are shown in Table 2.

TABLE II

| Example | Inhibition of mortality in % |
|---|---|
| 2 | 100 |
| 24 | 100 |
| 34 | 60 |
| 38 | 60 |
| 39 | 100 |
| 40 | 100 |

3. Activity as antagonist of the contraction of isolated guinea pig trachea

The compounds of the formula I are used as antagonists of the contraction of isolated guinea pig trachea. The agonists employed were $PGF_{2\alpha}$ (Upjohn, Germany), calcium ionophore A23187 (Calbiochem, Bad Soden, Germany), and substance P (American Peptide Comp., USA):

a) $PGF_{2\alpha PGF2\alpha}$ displays its contractile action via endogenous receptors. Inhibition of contractions which are induced by this cyclooxygenase product is only possible by competitive antagonism at the receptor or of the subsequent signal pathway.

b) Calcium ionophore A23187 (Calbiochem, Bad Soden) acts by increased uptake of calcium ions, and an activation of all calcium-dependent signal cascades in the cell. Lipoxygenase inhibitors, in particular, and generally antiinflammatory substances show effects in this model.

c) Substance P Substance P as a transmitter substance between the immune system and nervous system shows a contractile action against smooth musculature. The antagonism is possible on the one hand due to specific receptor antagonists, and on the other hand also due to inhibition of the subsequent signal pathway. Preparations which directly or indirectly increase the intracellular concentration of cyclic nucleotides in particular show spasmolytic properties here.

Preparation of the organ sections and experimental procedure:

The guinea pig is sacrificed by means of terminal laughing gas anaesthesia. The trachea is exposed along its entire length and cut into 15 individual cartilage rings. 5 rings in each case are tied together to give a chain and fixed in the organ bath under a preload of 3 g. After an equilibration time of 45 minutes, a contraction is produced using the agonist. The antagonist (test preparation) is added cumulatively on the plateau of the maximum. Evaluation is carried out in % force change relative to the contraction maximum. The experimental procedure is carried out at 37° C.; the physiological nutrient solution used is a modified Krebs-Henseleit solution through which is bubbled 95% by volume of $O_2$, 5% by volume of $CO_2$.

Experimental animals: albino guinea pigs (Hattersheim Animal Breeding Institute, Kastengrund, Germany), weight: 200 to 300 g, sex male or female.

| Composition of the organ bath (nutrient solution): Modified Krebs-Henseleit solution | | | |
|---|---|---|---|
| for the calcium ionophore A23187 | | for the agonist SP for the agonist $PGF_{2\alpha}$ | |
| NaCl | 6.9 g | NaCl | 7.9 g |
| $KH_2PO_4$ | 0.14 g | $KH_2PO_4$ | 0.18 g |
| $NaHCO_3$ | 2.1 g | $NaHCO_3$ | 1.37 g |

-continued

Composition of the organ bath (nutrient solution):
Modified Krebs-Henseleit solution

| for the calcium ionophore A23187 | | for the agonist SP for the agonist $PGF_{2\alpha}$ | |
|---|---|---|---|
| Glucose | 2.0 g | Glucose | 1.53 g |
| KCl | 0.35 g | KCl | 0.25 g |
| $CaCl_2$ | 0.28 g | $CaCl_2$ | 0.27 g |
| $MgSO_4$ | 0.14 g | to 1 l of double-distilled water | |
| to 1 l of double-distilled water | | | |

Vehicle: double-distilled water, ethanol or isopropanol; administration: into the organ bath number of administration: cumulative, in SP individual doses Results: An antagonistic action of the compounds according to the invention is seen with respect to KCl, prostaglandin $PGF_{2\alpha}$, calcium ionophore (A 23187) and substance P. The results are shown in Table 3.

TABLE 3

| | Anticontractile action (trachea) | | |
|---|---|---|---|
| Example | $PGF_{2\alpha}$ | Ca ionophore | SP antagonism |
| 2 | >10 | >10 | 10–30 |
| 4 | >10 | >10 | 10–30 |
| 9 | | | 10–30 |
| 15 | | | 30–60 |
| 17 | | | 30–60 |
| 20 | | | 10–30 |
| 23 | >10 | >10 | 10–30 |
| 24 | >10 | | 30–60 |
| 30 | >10 | 10 | 10–30 |
| 32 | | | 10–30 |
| 33 | | | 10–30 |
| 35 | | >10 | 30–60 |
| 38 | >10 | 10 | 10–30 |
| 47 | | | 10–30 |

All numerical values are indicated in the unit µg/ml and relate to the concentration range of the tested compound of the formula I according to the invention (see example numbers in Table 1) which is necessary in order to cause a dilatation which corresponds to the $ED_{50}$ range.

4. Activity as an antagonist of the contraction of isolated guinea pig lung strips The test carried out is based on the same principle as the test indicated in the pharmacological test 3; however, lung strips are used here.

Preparation of the organ sections and experimental procedure:

The guinea pig is sacrificed under laughing gas anaesthesia. The entire pulmonary tract is exposed starting from the trachea. The lobes of the lung are cut in a circular fashion such that 3 mm wide strips are formed. The strips of the upper lobes are divided in order to obtain a total of six approximately equal size strips. The strips are suspended in the organ baths under a preload of 4 g. The nutrient solutions used are modified Krebs Henseleit solutions. When using "Platelet activating factor" (PAF) as an antagonist, the composition of this solution corresponds to that for the agonist SP in "Test 3"; for the agonist $LTD_4$ a Krebs Henseleit solution as in the case of the agonist KCl (Test 3) is used. 95% by volume $O_2$, 5% by volume $CO_2$ is used for bubbling through the bath; the bath temperature is 37° C. The experimental procedure is carried out in a therapeutically cumulative methodology, using the dosage graduations 1, 3, 6 and 10 µg/ml.

The experimental animals, organ bath, vehicles and manner of administration correspond to that stated in pharmacological test 3.

Results: an antagonistic action of the compound of the formula I is seen with respect to "leukotriene $D_4$" ($LTD_4$) and the membrane lipid "Platelet activating factor". The results are shown in Table 4.

TABLE 4

| | Anticontractile action (lung) | |
|---|---|---|
| Example | PAF | $LTD_4$ |
| 1 | 3–9 | |
| 2 | 3–6 | 3–6 |
| 4 | 1–3 | |
| 7 | 3–6 | |
| 8 | 5–10 | |
| 9 | | 3–6 |
| 13 | 6–10 | |
| 17 | 1–3 | 1–3 |
| 23 | 1–3 | 1–3 |
| 25 | 5–15 | |
| 28 | 3–9 | |
| 30 | 3–6 | 6–10 |
| 31 | 6–10 | |
| 32 | 6–10 | 6–10 |
| 33 | 3–6 | |
| 35 | 3–6 | |
| 36 | 5–15 | |
| 37 | 1–3 | |
| 38 | 1–3 | |
| 39 | | 3–6 |
| 43 | 1–3 | 1–6 |
| 45 | 1–3 | |
| 49 | | 3–6 |
| 53 | 1–3 | |
| 54 | 1–3 | |
| 55 | 1–3 | |

All numerical values are indicated in the unit µg/ml and relate to the concentration range of tested compound of the formula I (see example numbers in Table 1) which is necessary in order to cause a contraction which corresponds to the $IC_{50}$ value.

5. Inhibition of phosphodiesterase III activity

The test is carried out using phosphodiesterase from Boehringer Mannheim (Mannheim, Germany), Order No. 108 243 according to the method of T. SAEKI, I. SAITO, Biochem. Pharm. 46, No. 5, (1986), pages 833–839.

The results are shown in Table 5.

| Example | PDE III Inhibition [%] |
|---|---|
| 2 | 65 |
| 17 | 77 |
| 20 | 65 |
| 23 | 65 |
| 32 | 65 |
| 34 | 82 |
| 39 | 65 |
| 41 | 56 |
| 43 | 52 |
| 46 | 67 |
| 47 | 64 |
| 48 | 52 |
| 49 | 57 |
| 50 | 51 |
| 55 | 59 |
| 57 | 70 |

All numerical values are indicated in % inhibition of the enzyme activity at 100 µM of the corresponding compound of the formula I.

What is claimed is:

1. A compound of the formula

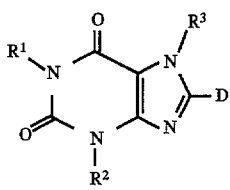

and/or a physiologically tolerable salt of the compound of the formula I and/or an optionally stereoisomeric form of the compound of the formula I, where $R^1$ and $R^3$ are identical or different and at least one of the radicals $R^1$ and $R^3$ is a) a radical of the formula XI

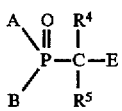

in which $R^4$ and $R^5$ are identical or different and independently of one another are
  1.1 a hydrogen atom,
  1.2 hydroxyl or
  1.3 $(C_1-C_6)$-alkyl, A and B are identical or different and independently of one another are
  2.1 $(C_1-C_4)$-alkyl,
  2.2 $(C_1-C_6)$-alkoxy,
  2.3 hydroxyl or
  2.4 benzyloxy, E is a covalent bond or a straight-chain or branched alkyl having 1 to 5 carbon atoms, and b) if only one of the radicals $R^1$ or $R^3$ have the meaning mentioned under a), the other radical $R^1$ or $R^3$ is
  1) a hydrogen atom,
  2) $(C_1-C_6)$-alkyl, straight-chain or branched,
  3) $(C_2-C_6)$-alkyl, straight-chain or branched, where the carbon chain is interrupted by 1 or 2 oxygen atoms and 2 oxygen atoms bonded to one another are excluded,
  4) $(C_1-C_8)$-alkyl, straight-chain or branched, substituted by
    4.1 an oxo group or
    4.2 one or two hydroxyl groups,
  5) $(C_2-C_6)$-alkenyl, straight-chain or branched,
  6) benzyl,
  7) benzyl, mono-to pentasubstituted by
    7.1 $(C_1-C_4)$-alkyl or
    7.2 $(C_1-C_4)$-alkoxy,
  8) $(C_3-C_6)$-cycloalkyl or
  9) $(C_1-C_4)$-alkyl-$(C_3-C_6)$-cycloalkyl, and $R^2$ is
  1) a hydrogen atom,
  2) $(C_1-C_6)$-alkyl, straight-chain or branched,
  3) $(C_2-C_6)$-alkyl, straight-chain or branched, the carbon chain being interrupted by 1 or 2 oxygen atoms and 2 oxygen atoms bonded to one another being excluded,
  4) benzyl,
  5) benzyl, mono- to pentasubstituted by
    5.1 $(C_1-C_4)$-alkyl or
    5.2 $(C_1-C_4)$-alkoxy,
  6) phenyl,
  7) $(C_3-C_6)$-cycloalkyl or
  8) $(C_1-C_4)$-alkyl-$(C_3-C_6)$-cycloalkyl, and D is
  1) a hydrogen atom or
  2) a fluorine, chlorine, bromine or iodine atom, the compounds diethyl [4-(1,3-dimethylxanthin-7-yl)butyl]-phosphonate, 5-(1,3-dimethoxyxanthin-7-yl) pentylphosphonic acid, 4-(1,3-dimethylxanthin-7-yl) butylphosphonic acid and 3-(1,3-dimethylxanthin-7-yl) propyl-phosphonic acid being excluded.

2. A compound of the formula I as claimed in claim 1, wherein A and B are
  1) hydroxyl,
  2) $C_2$-alkoxy or
  3) methyl.

3. A compound of the formula I as claimed in claim 1, wherein $R^2$ is
  1) a hydrogen atom,
  2) $(C_2-C_6)$-alkyl, straight-chain or branched, the carbon chain being interrupted by 1 oxygen atom,
  3) benzyl,
  4) cyclopropyl or
  5) —$CH_2$-cyclopropyl,.

4. A compound of the formula I as claimed in one or more of claims 1 to 3, wherein one of the radicals $R^1$ or $R^3$ is a radical of the formula XI and the other radical $R^1$ or $R^3$ is
  1) a hydrogen atom,
  2) $(C_2-C_6)$-alkyl, straight-chain or branched, the carbon chain being interrupted by 1 or 2 oxygen atoms and 2 oxygen atoms bonded to one another being excluded,
  3) benzyl or
  4) —$CH_2$-cyclopropyl.

5. A process for the preparation of the compound of the formula I as claimed in claim 1, which comprises
  A) reacting a compound of the formula III

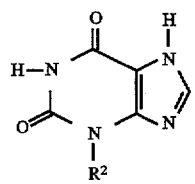

where
  $R^2$ has the meaning mentioned in formula I as claimed in claim 1, in the presence of basic agents with an alkylating agent of the formula II

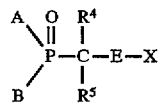

where X is chlorine, bromine, iodine or a sulfonic acid ester radical and $R^4$, $R^5$, A, B and E have the meaning mentioned in formula XI, to give a compound of the formula I, where $R^1$ is a hydrogen atom and $R^3$ is a radical of the formula XI

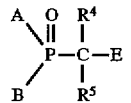

and $R^2$ has the meaning mentioned in formula I, or

B) reacting a compound of the formula I prepared according to A) in the presence of basic agents with an alkylating agent of the formula II, where X, $R^4$, $R^5$, A, B and E are defined as in process A), to give a compound of the formula I as claimed in claim 1, where $R^1$ and $R^3$ are identical or different and are a radical of the formula XI, or C) reacting a compound of the formula I prepared according to A) in the presence of basic agents with a compound $R^6$—X, where $R^6$ is
1) a hydrogen atom,
2) $(C_1-C_6)$-alkyl, straight-chain or branched,
3) $(C_2-C_6)$-alkyl, straight-chain or branched, where the carbon chain is interrupted by 1 or 2 oxygen atoms and 2 oxygen atoms bonded to one another are excluded,
4) $(C_1-C_6)$-alkyl, straight-chain or branched, substituted by
 4.1 an oxo group or
 4.2 one or two hydroxyl groups,
5) $(C_2-C_6)$-alkenyl, straight-chain or branched,
6) benzyl,
7) benzyl, mono- to pentasubstituted by
 7.1 $(C_1-C_4)$-alkyl or
 7.2 $(C_1-C_4)$-alkoxy,
8) $(C_3-C_6)$-cycloalkyl or
9) $(C_1-C_4)$-alkyl-$(C_3-C_6)$-cycloalkyl, and X has the meaning mentioned under A), to give a compound of the formula I as claimed in claim 1, where $R^1$ has the meaning of $R^6$, $R^2$ is defined according to the compound of the formula I and $R^3$ has the meaning of the formula II, or D) reacting a compound of the formula IV

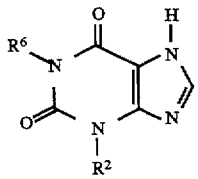

(IV)

where $R^6$ has the meaning mentioned under C) and $R^2$ has the meaning mentioned in formula I, in the presence of basic agents with an alkylating agent of the formula II to give a compound of the formula I, where $R^1$ has the meaning of $R^6$, and $R^2$ has the meaning mentioned in formula I and $R^3$ has the meaning mentioned in formula XI, or E) reacting a compound of the formula V

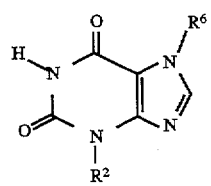

(V)

where $R^6$ has the meaning mentioned under C) and $R^2$ has the meaning mentioned in formula I, in the presence of basic agents with an alkylating agent of the formula II to give a compound of the formula I, where $R^1$ has the meaning mentioned in formula XI, $R^2$ has the meaning mentioned in formula I and $R^3$ has the meaning of $R^6$, or F) in a compound of the formula I, where at least one $R^1$, $R^2$ and $R^3$ is a benzyl, alkoxymethyl or alkoxyalkoxymethyl radical and at least one $R^1$ and $R^3$ is a radical of the formula XI, removing the benzyl, alkoxymethyl or alkoxyalkoxymethyl radical from the formula I under reducing or hydrolytic conditions, or G) reacting a compound of the formula VI

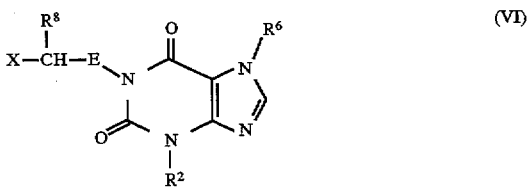

(VI)

where
$R^6$ has the meaning mentioned under C),
$R^2$ has the meaning mentioned in formula I,
E has the meaning mentioned in formula XI,
$R^8$ is a hydrogen atom or $(C_1-C_4)$-alkyl and
X is chlorine, bromine, iodine or a sulfonic acid ester radical, in the presence of a strong base such as sodium hydride, butyllithium or lithium diisopropylamide in an inert solvent with a compound of the formula VIII

(VIII)

where A and B have the meaning mentioned in formula I and $R^a$ is a hydrogen atom or $(C_1-C_4)$-alkyl, to give a compound of the formula I, where $R^1$ has the meaning mentioned in formula XI, $R^2$ has the meaning mentioned in formula I and $R^3$ has the meaning of $R^6$, or H) reacting a compound of the formula VI, where $R^2$, $R^6$, $R^8$, E and X have the meaning mentioned under G) with a compound of the formula IX

$P(OR^{10})_3$ (IX)

where P is phosphorus, O is oxygen and $R^{10}$ is a $(C_1-C_4)$-alkyl, to give a compound of the formula I, where $R^1$ has the meaning mentioned in formula XI, $R^2$ has the meaning mentioned in formula I and $R^3$ has the meaning of $R^6$, or I) converting a compound of the formula I where $R^1$, $R^2$, $R^3$, E and D have the meaning mentioned in formula I and A and B are $(C_1-C_4)$-alkyl or $(C_1-C_4)$-alkoxy, with agents such as mineral acids or silyl halides into the corresponding phosphonic acid derivatives of the formula I, or K) converting a compound of the formula I; where $R^1$, $R^2$, $R^3$, E and D have the meaning mentioned in formula I and A or B is a benzyloxy group, selectively into the corresponding phosphonic acid hemiesters, or L) halogenating a compound of the formula I, where $R^1$, $R^2$, $R^3$, E, A and B have the meaning mentioned in formula I and D is a hydrogen atom, a corresponding compound of the formula I being formed in which D is fluorine, chlorine, bromine or iodine, or M) isolating the compound of the formula I prepared according to processes A) to L) either in free form or, in the case of the presence of acidic or basic groups, optionally converting it into physiologically tolerable salts.

6. A pharmaceutical composition comprising an amount, effective for use as a pharmaceutical in the treatment of the reduced loss of function of the musculature, of a compound of the formula I, as claimed in claim 1, the compounds diethyl [4-(1,3-dimethylxanthin-7-yl)butyl]phosphonate, 5-(1,3-dimethoxy-xanthin-7-yl)pentylphosphonic acid, 4-(1,3-dimethylxanthin-7-yl)-butylphosphonic acid and 3-(1,3-dimethylxanthin-7-yl)propyl-phosphonic acid being excluded.

7. A pharmaceutical composition comprising an amount, effective for use as a pharmaceutical in the treatment of the reduced loss of function of the musculature, of a compound as claimed in claim 2.

8. A pharmaceutical composition comprising an amount, effective for use as a pharmaceutical in the treatment of the reduced loss of function of the musculature, of a compound as claimed in claim 3.

9. A pharmaceutical composition comprising an amount, effective for use as a pharmaceutical in the treatment of the reduced loss of function of the musculature, of a compound as claimed in claim 4.

10. A pharmaceutical composition comprising an amount, effective for use as a pharmaceutical for prophylaxis and therapy of muscular atrophy, of a compound of the formula I, as claimed in claim 1, the compounds diethyl [4-(1,3-dimethylxanthin-7-yl)butyl]phosphonate, 5-(1,3-dimethoxy-xanthin-7-yl)pentylphosphonic acid, 4-(1,3-dimethylxanthin-7-yl)-butylphosphonic acid and 3-(1,3-dimethylxanthin-7-yl)propyl-phosphonic acid being excluded.

11. A pharmaceutical composition comprising an amount, effective for use as a pharmaceutical in the treatment of muscular dystrophy, of a compound of the formula I, as claimed in claim 1, the compounds diethyl [4-(1,3-dimethylxanthin-7-yl)butyl]phosphonate, 5-(1,3-dimethoxy-xanthin-7-yl)pentylphosphonic acid, 4-(1,3-di methylxanthin-7-yl)-butylphosphonic acid and 3-(1,3-dimethylxanthin-7-yl)propyl-phosphonic acid being excluded.

12. A pharmaceutical composition comprising an amount, effective for use as a pharmaceutical in the treatment of inflammation of the bowel, of a compound of the formula I, as claimed in claim 1, the compounds diethyl [4-(1,3-dimethylxanthin-7-yl)butyl]phosphonate, 5-(1,3-dimethoxy-xanthin-7-yl)pentylphosphonic acid, 4-(1,3-dimethylxanthin-7-yl)-butylphosphonic acid and 3-(1,3-dimethylxanthin-7-yl)propyl-phosphonic acid being excluded.

13. A pharmaceutical composition comprising an amount, effective for use as a pharmaceutical in the treatment of, ulcerative colitis, as a result of infections, of a compound of the formula I, as claimed in claim 1, the compounds diethyl [4-(1,3-dimethylxanthin-7-yl)butyl]phosphonate, 5-(1,3-dimethoxy-xanthin-7-yl)pentylphosphonic acid, 4-(1,3-dimethylxanthin-7-yl)-butylphosphonic acid and 3-(1,3-dimethylxanthin-7-yl)propyl-phosphonic acid being excluded.

14. A method of treating a patient suffering from muscular atrophy comprising administering to the patient a pharmaceutical according to claim 6.

15. A method of treating a patient suffering from muscular dystrophy comprising administering to the patient a pharmaceutical according to claim 6.

16. A method of treating a patient suffering from inflammation of the bowel comprising administering to the patient a pharmaceutical according to claim 6.

17. A method of treating a patient suffering from ulcerative colitis, as a result of infections, comprising administering to the patient a pharmaceutical according to claim 6.

* * * * *

UNITED STATES PATENT AND TRADEMARK OFFICE
CERTIFICATE OF CORRECTION

PATENT NO. : 5,728,686
DATED : March 17, 1998
INVENTOR(S) : Gunter Billen et al.

It is certified that error appears in the above-identified patent and that said Letters Patent is hereby corrected as shown below:

Title Page, Item [57], in the Abstract, column 2, line 1, after "formula", insert --I--.

Claim 1, column 61, line 2, after "formula", insert--I--.

Claim 1, column 61, line 49, "mono-to" should read --mono- to--.

Claim 3, column 62, line 22, after "cyclopropyl", delete ",".

Claim 5, column 64, line 46, "I;" should read --I,--.

Signed and Sealed this

Twenty-ninth Day of June, 1999

Attest:

Q. TODD DICKINSON

*Attesting Officer*  *Acting Commissioner of Patents and Trademarks*